United States Patent
Murata et al.

(10) Patent No.: US 10,147,890 B2
(45) Date of Patent: Dec. 4, 2018

(54) PHOTOELECTRIC CONVERSION ELEMENT, SOLID-STATE IMAGING DEVICE, ORGANIC LIGHT-ABSORBING MATERIAL, AND ORGANIC LIGHT-ABSORBING MATERIAL INTERMEDIATE

(71) Applicant: SONY CORPORATION, Tokyo (JP)

(72) Inventors: Masaki Murata, Tokyo (JP); Miki Sudou, Kanagawa (JP); Hiroshi Nishihara, Tokyo (JP); Ryota Sakamoto, Tokyo (JP); Junko Kakinuma, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/311,623

(22) PCT Filed: Apr. 8, 2015

(86) PCT No.: PCT/JP2015/060918
§ 371 (c)(1),
(2) Date: Nov. 16, 2016

(87) PCT Pub. No.: WO2015/178116
PCT Pub. Date: Nov. 26, 2015

(65) Prior Publication Data
US 2017/0092876 A1  Mar. 30, 2017

(30) Foreign Application Priority Data
May 23, 2014  (JP) ................................ 2014-106900

(51) Int. Cl.
*H01L 51/00* (2006.01)
*C07D 209/88* (2006.01)
(Continued)

(52) U.S. Cl.
CPC ........ *H01L 51/0072* (2013.01); *C07D 209/88* (2013.01); *C07F 7/0812* (2013.01);
(Continued)

(58) Field of Classification Search
CPC ........ C07D 209/88; C07F 7/08; C07F 7/0812; H01L 27/30; H01L 51/00; H01L 27/146;
(Continued)

(56) References Cited

U.S. PATENT DOCUMENTS

2013/0134409 A1* 5/2013 Nihei .................. C07D 277/20
257/40
2016/0351810 A1* 12/2016 Umehara ............... C09K 11/06
(Continued)

FOREIGN PATENT DOCUMENTS

JP   2012-028739 A   9/2012
JP   2014-510726 A   5/2014

OTHER PUBLICATIONS

International Search Report prepared by the Japan Patent Office dated Jun. 24, 2015, for International Application No. PCT/JP2015/060918.

*Primary Examiner* — Thanh T Nguyen

(74) *Attorney, Agent, or Firm* — Sheridan Ross P.C.

(57) ABSTRACT

A photoelectric conversion element includes (a-1) a first electrode 21 and a second electrode 22 disposed apart from each other, and (a-2) a photoelectric conversion material layer 30 disposed between the first electrode 21 and the second electrode 22. The photoelectric conversion material layer 30 is formed of the following structural formula (1).
(Continued)

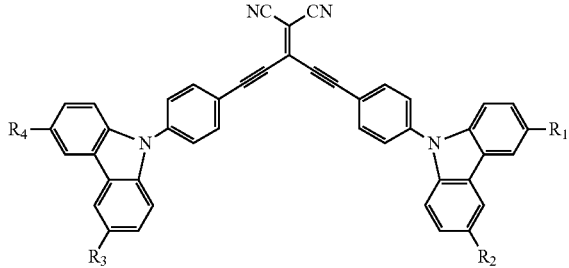

(1)

12 Claims, 11 Drawing Sheets

(51) Int. Cl.
*C09K 3/00* (2006.01)
*H01L 27/146* (2006.01)
*H01L 31/10* (2006.01)
*C07F 7/08* (2006.01)
*H01L 27/30* (2006.01)
*H01L 51/42* (2006.01)

(52) U.S. Cl.
CPC .............. *C09K 3/00* (2013.01); *H01L 27/146* (2013.01); *H01L 27/307* (2013.01); *H01L 31/10* (2013.01); *H01L 51/0051* (2013.01); *H01L 51/4253* (2013.01); *H01L 51/42* (2013.01); *Y02E 10/549* (2013.01)

(58) Field of Classification Search
CPC ... H01L 27/307; H01L 31/10; H01L 51/0051; H01L 51/0072; H01L 51/4253; H01L 51/42; C09K 3/00; Y02E 10/549
See application file for complete search history.

(56) References Cited

U.S. PATENT DOCUMENTS

2017/0373258 A1* 12/2017 Obana ................ H01L 51/0072
2018/0151624 A1* 5/2018 Hasegawa .......... H01L 51/0072

* cited by examiner 3,6-DIBROMO-9H-CARBAZOLE 3,6-DIMETHOXY-9H-CARBAZOLE 9-(4-BROMOPHENYL)3,6-DIMETHOXY-9H-CARBAZOLE 9-(4-ETHYNYLPHENYL)-3,6-DIMETHOXY-9H-CARBAZOLE 1,5-BIS(4-(3,6-DIMETHOXY-9H-CARBAZOL-9-YL)PHENYL)PENTA-1,4-DIYNE-3-OL 1,5-BIS(4-(3,6-DIMETHOXY-9H-CARBAZOL-9-YL)PHENYL)PENTA-1,4-DIYNE-3-ON 2-(3-[4-(DIMETHOXYCARBAZOLE)PHENYL]-1-
{[4-(DIMETHOXYCARBAZOLE)PHENYL]ETHYNYL}-2-YNYLIDENE

PHOTOELECTRIC CONVERSION ELEMENT, SOLID-STATE IMAGING DEVICE, ORGANIC LIGHT-ABSORBING MATERIAL, AND ORGANIC LIGHT-ABSORBING MATERIAL INTERMEDIATE

CROSS REFERENCE TO RELATED APPLICATIONS

This application is a national stage application under 35 U.S.C. 371 and claims the benefit of PCT Application No PCT/JP2015/060918 having an international filing claimed the benefit of Japanese Patent Application No. 2014-106000 filed 23 May 2014, the disclosures of which are incorporated herein by reference in their entirety.

TECHNICAL FIELD

The present disclosure relates to a photoelectric conversion element, a solid-state imaging device, an organic light-absorbing material, and an organic light-absorbing material intermediate.

BACKGROUND ART

A photoelectric conversion element (organic photodiode) using an organic material can photoelectrically convert only a specific color (wavelength band). And because of such a characteristic, when the photoelectric conversion element is used as a photoelectric conversion element in a solid-state imaging device, it is possible to obtain a structure having sub-pixels laminated, not possible with a conventional solid-state imaging device in which each of sub-pixels is formed of a combination of an on-chip color filter (OCCF) and a photoelectric conversion element and the sub-pixels are arranged two-dimensionally. Therefore, the photoelectric conversion element can receive incident light with a high efficiency, and therefore a higher sensitivity of the solid-state imaging device can be expected. In addition, there is an advantage that a false color is not generated because demosaic processing is not required.

An organic photodiode used in an imaging device or an imaging element has a structure the same as or similar to various organic thin-film solar cells. Conventionally, as a structure of the organic photodiode, a structure using a p-n junction or a p-i-n junction (for example, refer to JP-2006-33942 A), a structure using a bulk heterostructure (refer to JP 2007-123707 A), and a structure using a buffer layer (for example, refer to JP 2007-311647 A and JP 2007-088033 A) are known, and are exclusively intended to improve a photoelectric conversion efficiency.

CITATION LIST

Patent Document

Patent Document 1: JP 2006-33942 A
Patent Document 2: JP 2007-123707 A
Patent Document 3: JP 2007-311647 A
Patent Document 4: JP 2007-088033 A

Non-Patent Document

Non-Patent document 1: Chem. Rev. 107, 953 (2007)

SUMMARY OF THE INVENTION

Problems to be Solved by the Invention

By the way, a diffusion distance of an exciton of most organic materials is 20 nm or less, and a conversion efficiency of the organic photodiode is generally lower than that of an inorganic solar cell typified by a silicon solar cell. And in general, an organic material has a higher resistance, a lower mobility, and a lower carrier density than a silicon semiconductor material (for example, refer to Chem. Rev. 107, 953 (2007)). Therefore, the organic photodiode has not achieved a characteristic comparable to a conventional photodiode using an inorganic material typified by silicon in a sensitivity and a response property. However, some organic materials have a higher absorption coefficient than the photodiode using a silicon semiconductor material, and a high sensitivity can be expected in a photodiode using these organic materials. In silicon, the absorption coefficient is a physical quantity uniquely defined. Therefore, in the photodiode using a silicon semiconductor material, a characteristic cannot be improved by the absorption coefficient.

Therefore, an object of the present disclosure is to provide a photoelectric conversion element using an organic material having an excellent light absorption characteristic, a solid-state imaging device including the photoelectric conversion element, and an organic light-absorbing material and an intermediate thereof suitable for use in the photoelectric conversion element.

Solutions to Problems

A photoelectric conversion element of the present disclosure in order to achieve the above object includes:
(a-1) a first electrode and a second electrode disposed apart from each other; and
(a-2) a photoelectric conversion material layer disposed between the first electrode and the second electrode, and
the photoelectric conversion material layer is formed of the following structural formula (1).

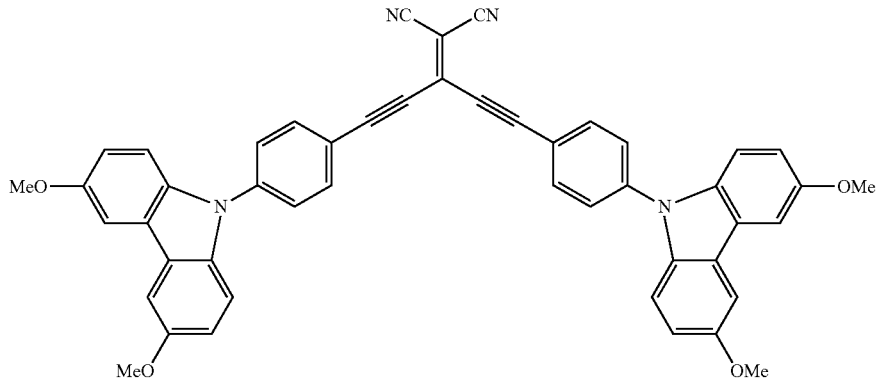

(1)

Here, $R_1$, $R_2$, $R_3$, and $R_4$ are each independently a hydrogen atom or a substituent selected from the group consisting of an alkyl group, a cycloalkyl group, an alkenyl group, an alkynyl group, an aryl group, an arylalkyl group, an aromatic heterocyclic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureido group, a sulfinyl group, an alkylsulfonyl group, an arylsulfonyl group, an amino group, a halogen atom, a fluorinated hydrocarbon group, a cyano group, a nitro group, a hydroxy group, a mercapto group, a silyl group, a nitroso group, a cyanide (nitrile) group, an isocyanide (isonitrile) group, a thiocyanate group, an isothiocyanate group, an aldehyde group, a thioaldehyde group, a keto group, thioketo group, and a hydrazide group. Incidentally, each of these substituents may be a partially substituted group or an unsubstituted group.

A solid-state imaging device of the present disclosure in order to achieve the above object includes:

(a-1) a first electrode and a second electrode disposed apart from each other; and (a-2) a photoelectric conversion material layer disposed between the first electrode and the second electrode, and the photoelectric conversion material layer includes the photoelectric conversion element formed of the above structural formula (1).

An organic light-absorbing material of the present disclosure in order to achieve the above object is formed of the above structural formula (1).

An organic light-absorbing material intermediate according to a first aspect of the present disclosure in order to achieve the above object is formed of the following structural formula (2).

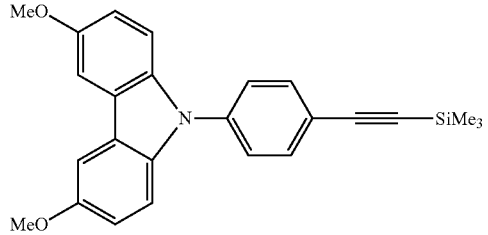

(2)

An organic light-absorbing material intermediate according to a second aspect of the present disclosure in order to achieve the above object is formed of the following structural formula (3).

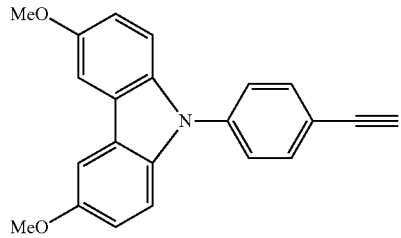

(3)

An organic light-absorbing material intermediate according to a third aspect of the present disclosure in order to achieve the above object is formed of the following structural formula (4).

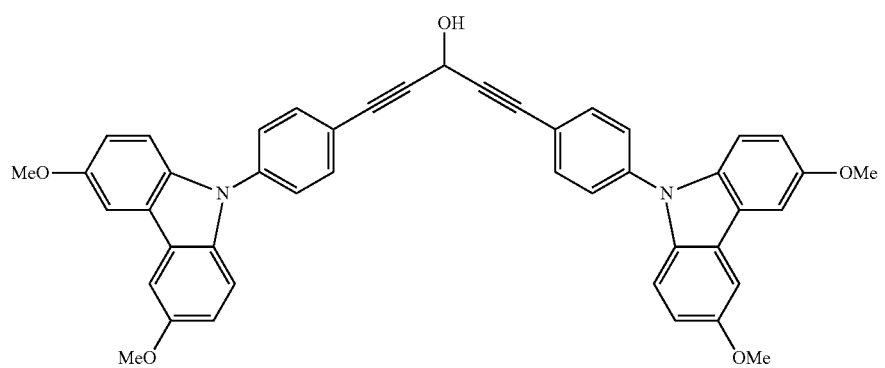

(4)

An organic light-absorbing material intermediate according to a fourth aspect of the present disclosure in order to achieve the above object is formed of the following structural formula (5).

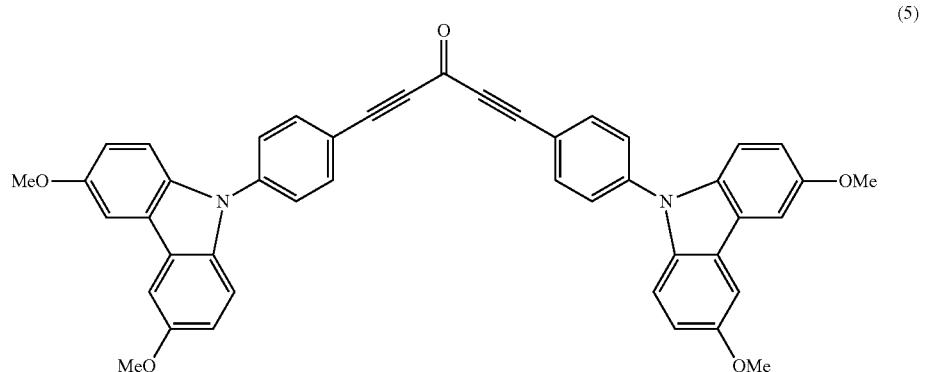 [SMILES: COc1ccc2c(c1)c1cc(OC)ccc1n2-c1ccc(C#CC(=O)C#Cc2ccc(-n3c4ccc(OC)cc4c4cc(OC)ccc43)cc2)cc1]

(5)

Effects of the Invention

In the present disclosure, a photoelectric conversion material layer has structural formula (1), that is, a malononitrile skeleton (dicyanoethylene skeleton) and a carbazole skeleton. Here, by imparting the malononitrile skeleton and the carbazole skeleton, an excellent light absorption characteristic can be imparted. And as a result, a photoelectric conversion element using an organic material having an excellent light absorption characteristic, a solid-state imaging device including the photoelectric conversion element, an organic light absorbing material suitable for use in the photoelectric conversion element, and an organic light-absorbing material intermediate can be provided. In addition, the organic material represented by the structural formula has a high absorption coefficient (α). Therefore, it is possible to reduce the thickness of the photoelectric conversion material layer, to solve a problem such as a high resistance, a low mobility, or a low carrier density which has been a disadvantage of a conventional organic material, and to provide a photoelectric conversion element or a solid-state imaging device having a high sensitivity and a high-speed response property. Incidentally, by reducing the thickness of the photoelectric conversion material layer, an electric field intensity E applied to the photoelectric conversion material layer can be increased upon application of the same potential, and a high photocurrent can be obtained even if the mobility or the carrier density is low. Furthermore, the degree of freedom in molecular design is high, and many derivatives can be designed. In addition, the photoelectric conversion material layer does not require an on-chip color filter because the photoelectric conversion material layer absorbs light having a specific wavelength, and a multilayer photoelectric conversion element can be achieved. Incidentally, the effects described herein are merely illustrative, and are not restrictive. In addition, an additional effect may be present.

BRIEF DESCRIPTION OF DRAWINGS

FIG. 9 is $^1$H NMR spectral data of 1,5-bis(4-(3,6-dimethoxy-9H-carbazol-9-yl)phenyl)penta-1,4-diyne-3-on.

MODE FOR CARRYING OUT THE INVENTION

Figure 1:
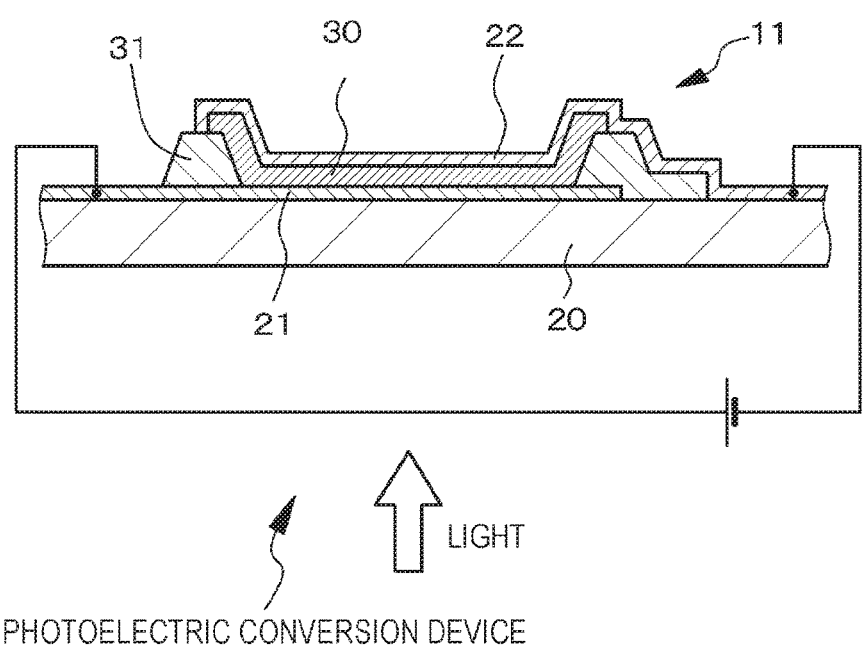
FIG. 1 is a schematic cross sectional view of a photoelectric conversion element in Example 2.

Hereinafter, the present disclosure will be described on the basis of Examples with reference to the drawings. However, the present disclosure is not limited to Examples, but various numerical values and materials in Examples are illustrative. Incidentally, description will be made in the following order.
1. General description concerning photoelectric conversion element, solid-state imaging device, organic light-absorbing material, and organic light-absorbing material intermediate of the present disclosure.
2. Example 1 (organic light-absorbing material and organic light-absorbing material intermediate of the present disclosure)
3. Example 2 (photoelectric conversion element and solid-state imaging device of the present disclosure) and others

[General Description Concerning Photoelectric Conversion Element, Solid-State Imaging Device, Organic Light-Absorbing Material, and Organic Light-Absorbing Material Intermediate of the Present Disclosure]

In a photoelectric conversion element of the present disclosure or a photoelectric conversion element in a solid-state imaging device of the present disclosure (hereinafter, these photoelectric conversion elements will be collectively referred to as "photoelectric conversion element or the like of the present disclosure"), $R_1$, $R_2$, $R_3$, and $R_4$ are each independently preferably an alkoxy group. In this case, $R_1$, $R_2$, $R_3$, and $R_4$ more preferably satisfy $R_1=R_3=R_2=R_4$, and $R_1$, $R_2$, $R_3$, and $R_4$ are each still more preferably a methoxy group. Alternatively, in the photoelectric conversion element or the like of the present disclosure, $R_1$, $R_2$, $R_3$, and $R_4$ preferably satisfy $R_1=R_3$ and $R_2=R_4$, and in this case, $R_1$, $R_2$, $R_3$, and $R_4$ more preferably satisfy $R_1=R_3=R_2=R_4$.

In the above-described photoelectric conversion element or the like of the present disclosure including a preferable embodiment, an electrode on a light incident side is preferably formed of a transparent conductive material. Such an electrode is referred to as "a transparent electrode". Here, examples of a transparent conductive material forming the transparent electrode include an indium-tin oxide (including ITO, Sn-doped $In_2O_3$, crystalline ITO, and amorphous ITO), IFO (F-doped $In_2O_3$), tin oxide ($SnO_2$), ATO (Sb-doped $SnO_2$), FTO (F-doped $SnO_2$), zinc oxide (including Al-doped, ZnO, B-doped ZnO, and Ga-doped ZnO), indium oxide-zinc oxide (IZO), titanium oxide ($TiO_2$), a spinel-type oxide, and an oxide having a $YbFe_2O_4$ structure. Although depending on a material forming a transparent electrode, examples of a method for forming a transparent electrode include a physical vapor deposition method (PVD method) including a vacuum vapor deposition method, a reactive vapor deposition method, various sputtering methods, an electron beam vapor deposition method, and an ion plating method, a chemical vapor deposition method (CVD method) including a pyrosol method, a method for thermally decomposing an organic metal compound, a spray method, a dipping method, and a MOCVD method, an electroless plating method, and an electrolytic plating method. In some cases, the other electrode may be also formed of a transparent conductive material.

In a case where transparency is not necessary, as a conductive material forming the first electrode or the second electrode, when the first electrode or the second electrode is caused to act as a cathode electrode, that is, when the first electrode or the second electrode is caused to act as an electrode for taking out a hole, the first electrode or the second electrode is preferably formed of a conductive material having a high work function (for example, $\varphi=4.5$ eV to 5.5 eV). Specific examples thereof include gold (Au), silver (Ag), chromium, (Cr), nickel (Ni), palladium (Pd), platinum (Pt), iron (Fe), iridium (Ir), germanium (Ge), osmium, (Os), rhenium (Re), and tellurium (Te). On the other, when the first electrode or the second electrode is caused to act as an anode, that is, when the first electrode or the second electrode is caused to act as an electrode for taking out an electron, the first electrode or the second electrode is preferably formed of a conductive material having a low work function (for example, $\varphi=3.5$ eV to 4.5 eV). Specific examples thereof include an alkali metal (for example, Li, Na, or K), a fluoride thereof, an oxide thereof, an alkaline earth metal (for example, Mg or Ca), a fluoride thereof, an oxide thereof, aluminum (Al), zinc (Zn), tin (Sn), thallium (Tl), a sodium-potassium alloy, an aluminum-lithium alloy, a magnesium-silver alloy, a rare earth metal such as indium or ytterbium, and an alloy thereof. Alternatively, examples of the material forming the first electrode or the second electrode include a metal such as platinum (Pt), gold (Au), palladium (Pd), chromium (Cr), nickel (Ni) aluminum (Al), silver (Ag), tantalum (Ta), tungsten (W), copper (Cu), titanium (Ti), indium (In), tin (Sn), iron (Fe), cobalt (Co), or molybdenum (Mo), an alloy containing these metal elements, a conductive particle formed of these metals, a conductive particle of an alloy containing these metals, a polysilicon containing impurities, a carbon material, an oxide semiconductor, and a conductive material such as a carbon nanotube or graphene. A lamination structure of layers containing these elements can be also used. Furthermore, examples of the material forming the first electrode or the second electrode include an organic material (conductive polymer) such as poly(3,4-ethylenedioxythiophene)/polystyrene sulfonic acid [PEDOT/PSS]. In addition, these conductive materials may be mixed with a binder (polymer) to form a paste or an ink, and the paste or the ink may be cured to be used as an electrode.

Although depending on a material forming the first electrode or the second electrode, examples of a method for forming the first electrode or the second electrode include various PVD methods described below; various CVD methods including an MOCVD method; various coating methods described below; a lift-off method; a sol-gel method; an electrodeposition method; a shadow mask method; a plating method such an electrolytic plating method, an electroless plating method, or a combination thereof; and a combination of any spraying method and a patterning technique, if necessary.

Furthermore, in the photoelectric conversion element or the like of the present disclosure including the preferable embodiment and configuration described above, a wavelength ($\lambda_{max}$) of a light absorption peak in a light absorption spectrum of the photoelectric conversion material layer (or the organic light-absorbing material or an organic light-absorbing material solution) can be 550±50 nm.

Furthermore, in the photoelectric conversion element or the like of the present disclosure including the preferable embodiment and configuration described above, the light absorption spectrum of the photoelectric conversion material layer (or the organic light-absorbing material or the organic light-absorbing material solution) can have one maximum value in a wavelength range of 500 nm to 600 nm.

Furthermore, in the photoelectric conversion element or the like of the present disclosure including the preferable embodiment and configuration described above, an absorption coefficient $\alpha$ ($cm^{-1}$) of the photoelectric conversion material layer (or an organic light-absorbing material thin film) is $1\times10^4$ or more, and preferably $1.5\times10^4$ or more. In addition, a molar absorption coefficient $\varepsilon$ ($dm^3 \cdot mol^{-1} \cdot cm^{-1}$) of the photoelectric conversion material layer (or the organic light-absorbing material solution) is $1\times10^4$ $dm^3 \cdot mol^{-1} \cdot cm^{-1}$ or more, and preferably $1.8\times10^4$ $dm^3 \cdot mol^{-1} \cdot cm^{-1}$ or more.

Furthermore, in the photoelectric conversion element or the like of the present disclosure including the preferable embodiment and configuration described above, a sublimation temperature of a material forming the photoelectric conversion material layer (or the organic light-absorbing material) is preferably 250° C. or higher.

As a molecular weight of the organic light-absorbing material of the present disclosure, 2000 or less, preferably 500 to 1500, and more preferably 500 to 1000 can be exemplified. In addition, "a bulk hetero layer" described below is a layer formed of a mixed layer including either a p-type organic light-absorbing material or an n-type organic light-absorbing material. The p-type organic light-absorbing material or organic transparent material and/or the n-type organic light-absorbing material or organic transparent material are/is formed of the organic light-absorbing material or the like of the present disclosure.

Examples of a p-type organic light-absorbing material or organic transparent material and/or an n-type organic light-absorbing material or organic transparent material other than the organic light-absorbing material or the like of the present disclosure include an aromatic monocyclic compound, an aromatic condensed ring compound, a heteromonocylic compound, a fused heterocyclic compound, a polymethine compound, a π conjugated low-molecular compound, a carbonium compound, a styryl compound, a stilbene compound, a metal complex compound, a π conjugated polymer compound, a σ conjugated compound, a dye-containing polymer compound, and a polymer complex compound.

Specific examples of the aromatic monocyclic compound include a triallyl amine compound and a derivative thereof, a biphenyl compound and a derivative thereof, and a diphenoquinone compound and a derivative thereof.

Specific examples of the aromatic condensed ring compound include an acene compound typified by naphthalene, anthracene, or pentacene and a derive thereof, a rubrene compound and a derivative thereof, a phenanthrene compound and a derivative thereof, a fluoranthene compound and a derivative thereof, a triphenylene compound and a derivative thereof, a pyrene compound and a derivative thereof, a chrysene compound and a derivative thereof, a perylene compound and a derivative thereof, a coronene compound and a derivative thereof, an indene compound and a derivative thereof, a bianthryl compound and a derivative thereof, a trianthrylene compound and a derivative thereof, a fluoranthene compound and a derivative thereof, an aceanthrylene compound and a derivative thereof, a pentaphene compound and a derivative thereof, a tetraphenylene compound and a derivative thereof, a peropyrene compound and a derivative thereof, a terrylene compound and a derivative thereof, bisanthrylene compound and a derivative thereof, a quarterterrylene compound and a derivative thereof, an indane compound and a derivative thereof, and a rubicene compound and a derivative thereof.

Specific examples of the heteromonocyclic compound include a thiophene compound and a derivative thereof, a pyrazoline compound and a derivative thereof, an azole compound and a derivative thereof, an oxazole compound and a derivative thereof, an oxadiazole compound and a derivative thereof, a pyran compound and a derivative thereof, a thiopyran compound and a derivative thereof, a pyrazine compound and a derivative thereof, a thiazole compound and a derivative thereof, a pyrrole compound and a derivative thereof, a triazole compound and a derivative thereof, a squarylium compound and a derivative thereof, a lactam compound and a derivative thereof, an azobenzene compound and a derivative thereof, a quinone compound and a derivative thereof, a furan compound and a derivative thereof, an azole compound and a derivative thereof, a pyrrolidone compound and a derivative thereof, a silole compound and a derivative thereof, an oxazolone compound and a derivative thereof, an imidazole compound and a derivative thereof, a pyrazoline compound and a derivative thereof, a pyridine compound and a derivative thereof, a bipyridine compound and a derivative thereof, a pyridazine compound and a derivative thereof, a dithiol compound and a derivative thereof, and a dioxyborane compound and a derivative thereof.

Specific examples of the fused heterocyclic compound include a pyrrolo pyrrole compound and a derivative thereof, a diazabicyclo compound and a derivative thereof, a phthalide compound and a derivative thereof, a benzoxazole compound and a derivative thereof, a benzothiophene compound and a derivative thereof, a benzothiazole compound and a derivative thereof, an indole compound and a derivative thereof, an imidazopyridine compound and a derivative thereof, a benzoazole compound and a derivative thereof, a benzopyran compound and a derivative thereof, a coumarin compound and a derivative thereof, a chromone compound and a derivative thereof, an azacoumarin compound and a derivative thereof, a quinolone compound and a derivative thereof, a benzoxazine compound and a derivative thereof, a phthalazine compound and a derivative thereof, a quinazoline compound and a derivative thereof, a quinoxaline compound and a derivative thereof, a pyrimidopyrimidine compound and a derivative thereof, a dibenzofuran compound and a derivative thereof, a carbazole compound and a derivative thereof, a pyrazoquinoline compound and a derivative thereof, a naphthalimide compound and a derivative thereof, a benzoquinoline compound and a derivative thereof, a phenanthridine compound and a derivative thereof, a phenanthroline compound and a derivative thereof, a phenazine compound and a derivative thereof, a pyridoquinoline compound and a derivative thereof, a dipyrimidopyrimidine compound and a derivative thereof, a teazaflavin compound and a derivative thereof, a dioxazine compound and a derivative thereof, a pyrimido quinazoline compound and a derivative thereof, a phenanthazole compound and a derivative thereof, a pyridoimidazo quinoxaline compound and a derivative thereof, a benzophenoxazone compound and a derivative thereof, a thioepindolidione compound and a derivative thereof, an epindolidione compound and a derivative thereof, a thioquinacridone compound and a derivative thereof, a quinacridone compound and a derivative thereof, a triphenodioxazine compound and a derivative thereof, a perinone compound and a derivative thereof, a Pechmann dye compound and a derivative thereof, a naphthyridine compound and a derivative thereof, a benzofuropyradine compound and a derivative thereof, an azathioxanthene compound and a derivative thereof, and an azathioxanthene compound and a derivative thereof.

Specific examples of the polymethine compound include a methine compound and a derivative thereof, a polymethine compound and a derivative thereof, a merocyanine compound and a derivative thereof, a hemicyanine compound and a derivative thereof, a streptocyanine compound and a derivative thereof, an oxanol compound and a derivative thereof, a pyrylium compound and a derivative thereof, and a cyanine compound and a derivative thereof. More specific examples thereof include phthalocyanine and a derivative thereof, subphthalocyanine and a derivative thereof, and dipyrin and a derivative thereof.

Specific examples of the π conjugated low-molecular compound include a dicyanomethylene compound and a derivative thereof and a malenonitrile compound and a derivative thereof. Specific examples of the carbonium compound include a xanthene compound and a derivative thereof, a rhodamine compound and a derivative thereof, an acridine compound and a derivative thereof, a thioxanthene compound and a derivative thereof, and an acridone compound and a derivative thereof. Specific examples of the styryl compound include a monofunctional styryl compound and a derivative thereof, a polyfunctional styryl compound and a derivative thereof, and a tetrabutyl butadiene compound and a derivative thereof. Specific examples of the stilbene compound include a stilbene compound and a derivative thereof, an azomethine compound and a derivative thereof, an azobenzene compound and a derivative thereof, and a fluoroscein compound and a derivative thereof. Specific examples of the metal complex compound include a Schiff base compound and a derivative thereof, a poriphyrin compound and a derivative thereof, a metallo poriphyrin compound and a derivative thereof, a metallo dipyrin compound and a derivative thereof, a lanthanoid compound and a derivative thereof, a metallo phthalocyanine compound and a derivative thereof, and a hydroxyquinolilato complex compound and a derivative thereof. More specific examples thereof include a tris(8-quinolinolato) metal complex typified by tris (8-quinolinolato) aluminum and a derivative thereof. Specific examples of the π conjugated polymer compound include a PPV compound and a derivative thereof, an oligothiophene compound and a derivative thereof, a polythiophene compound and a derivative thereof, and a polyalkyl fluorene compound and a derivative thereof. Specific examples of the σ conjugated compound include an oligosilane compound and a derivative thereof and a polysilane compound and a derivative thereof. Specific examples of the other compounds include an indigo compound and a derivative thereof, a thioindigo compound and a derivative thereof, a spiran compound and a derivative thereof, a silane compound and a derivative thereof, and a boron compound and a derivative thereof.

In the photoelectric conversion element or the like of the present disclosure, a first buffer layer/the photoelectric conversion material layer/a second buffer layer can be formed between the first electrode and the second electrode. Specifically, for example, the following configuration can be used.

the first buffer layer:
an n-type organic material layer (organic dye material or organic transparent material)
the photoelectric conversion material layer:
the p-type organic light-absorbing material of the present disclosure, or
the n-type organic light-absorbing material of the present disclosure, or
a mixed material of the p-type organic light-absorbing material of the present disclosure and an n-type organic transparent material, or
a mixed material of the n-type organic light-absorbing material of the present disclosure and a p-type organic transparent material, or
a bulk hetero layer
the second buffer layer:
a p-type organic material layer (organic dye material or organic transparent material)

Examples of the n-type organic material (organic dye material or organic transparent material) forming the first buffer layer include an aromatic ring compound and a hydrazone compound in addition to an n-type organic light-absorbing material or organic transparent material other than the above organic light-absorbing material or organic transparent material or the like of the present disclosure. Specific examples of the aromatic ring compound include a monoamine compound and a derivative thereof, an alkylene bond compound and a derivative thereof, an arylene bond compound and a derivative thereof, a phenylenesiamine compound and a derivative thereof, and a starburst compound and a derivative thereof. In addition, specific examples of the other compounds include a metal typified by Ca, Mg, Li, Ag, or Al and inorganic compounds of these metals (specifically, halides, oxides, and complex compounds of these metals).

Examples of the organic light-absorbing material or the organic transparent material forming the photoelectric conversion material layer include an aromatic ring compound, a hydrazone compound, an alicyclic compound, an aromatic ring compound, and a heterocyclic compound in addition to the organic light-absorbing material or organic transparent material or the like of the present disclosure, and a p-type organic light-absorbing material or organic transparent material and/or an n-type organic light-absorbing material or organic transparent material other than the above organic light-absorbing material or organic transparent material or the like of the present disclosure. Specific examples of the aromatic ring compound include a monoamine compound and a derivative thereof, an alkylene bond compound and a derivative thereof, arylene bond compound and a derivative thereof, a phenylenesiamine compound and a derivative thereof, and a starburst compound and a derivative thereof. Specific examples of the alicyclic compound, include a cyclopentadiene compound a derivative thereof. Specific examples of the aromatic ring compound include a tetraphenyl butadiene compound and a derivative thereof, a p-phenylene compound and a derivative thereof, and a fluoronylidene methane compound and a derivative thereof. Specific examples of the heterocyclic compound include a thiadiazopyridine compound and a derivative thereof, a pyrrolopyridine compound and a derivative thereof, a germacyclopentadiene compound and a derivative thereof, a benzazole compound and a derivative thereof, and a terrylenimide compound and a derivative thereof.

Examples of the p-type organic material (organic dye material or organic transparent material) forming the second buffer layer include an alicyclic compound, an aromatic ring compound, and a heterocyclic compound in addition to a p-type organic light-absorbing material or organic transparent material other than the above organic light-absorbing material or organic transparent material or the like of the present disclosure. Specific examples of the alicyclic compound include a cyclopentadiene compound a derivative thereof. Specific examples of the aromatic ring compound include a tetraphenyl butadiene compound and a derivative thereof, a p-phenylene compound and a derivative thereof, and a fluoronylidene methane compound and a derivative thereof. Specific examples of the heterocyclic compound include a thiadiazopyridine compound and a derivative thereof, a pyrrolopyridine compound and a derivative thereof, a germacyclopentadiene compound and a derivative thereof, a benzazole compound and a derivative thereof, and a terrylenimide compound and a derivative thereof.

Alternatively, in the photoelectric conversion element or the like of the present disclosure, the first buffer layer/the n-type organic material layer/the photoelectric conversion material layer/the p-type organic material layer/the second buffer layer can be formed between the first electrode and the second electrode. Specifically, for example, the following configuration can be used.

the first buffer layer:
an n-type organic material layer (organic dye material or organic transparent material)
the n-type organic material layer:
an organic dye material or an organic transparent material
the photoelectric conversion material layer:
the p-type organic light-absorbing material of the present disclosure, or
the n-type organic light-absorbing material of the present disclosure, or
a mixed material of the p-type organic light-absorbing material of the present disclosure and an n-type organic transparent material, or
a mixed material of the n-type organic light-absorbing material of the present disclosure and a p-type organic transparent material, or a bulk hetero layer the p-type organic material layer:

an organic dye material or an organic transparent material the second buffer layer:

a p-type organic material layer (organic dye material or organic transparent material)

Examples of the n-type organic material layer (organic dye material or organic transparent material) forming the first buffer layer include an aromatic ring compound and a hydrazone compound in addition to an n-type organic light-absorbing material or organic transparent material other than the above organic light-absorbing material or organic transparent material or the like of the present disclosure. Specific examples of the aromatic ring compound include a monoamine compound and a derivative thereof, an alkylene bond compound and a derivative thereof, an arylene bond compound and a derivative thereof, a phenylenesiamine compound and a derivative thereof, and a starburst compound and a derivative thereof. In addition, specific examples of the other compounds include a metal typified by Ca, Mg, Li, Ag, or Al and inorganic compounds of these metals (specifically, halides, oxides, and complex compounds of these metals).

Examples of the organic dye material or the organic transparent material forming the n-type organic material layer include an aromatic ring compound and a hydrazone compound in addition to an n-type organic light-absorbing material or organic transparent material other than the above organic light-absorbing material or organic transparent material or the like of the present disclosure. Specific examples of the aromatic ring compound include a monoamine compound and a derivative thereof, an alkylene bond compound and a derivative thereof, an arylene bond compound and a derivative thereof, a phenylenesiamine compound and a derivative thereof, and a starburst compound and a derivative thereof.

Examples of the organic light-absorbing material or the organic transparent material forming the photoelectric conversion material layer include an aromatic ring compound, a hydrazone compound, an alicyclic compound, an aromatic ring compound, and a heterocyclic compound in addition to the organic light-absorbing material or organic transparent material or the like of the present disclosure, and a p-type organic light-absorbing material or organic transparent material and/or an n-type organic light-absorbing material or organic transparent material other than the above organic light-absorbing material or organic transparent material or the like of the present disclosure. Specific examples of the aromatic ring compound include a monoamine compound and a derivative thereof, an alkylene bond compound and a derivative thereof, an arylene bond compound and a derivative thereof, a phenylenesiamine compound and a derivative thereof, and a starburst compound and a derivative thereof. Specific examples of the alicyclic compound include a cyclopentadiene compound a derivative thereof. Specific examples of the aromatic ring compound include a tetraphenyl butadiene compound and a derivative thereof, a p-phenylene compound and a derivative thereof, and a fluoronylidene methane compound and a derivative thereof. Specific examples of the heterocyclic compound include a thiadiazopyridine compound and a derivative thereof, a pyrrolopyxidine compound and a derivative thereof, a germacyclopentadiene compound and a derivative thereof, a benzazole compound and a derivative thereof, and a terrylenimide compound and a derivative thereof.

Examples of the organic dye material or the organic transparent material forming the p-type organic material layer include an alicyclic compound, an aromatic ring compound, and a heterocyclic compound in addition to a p-type organic light-absorbing material or organic transparent material other than the above organic light-absorbing material or organic transparent material or the like of the present disclosure. Specific examples of the alicyclic compound include a cyclopentadiene compound a derivative thereof. Specific examples of the aromatic ring compound include a tetraphenyl butadiene compound and a derivative thereof, a p-phenylene compound and a derivative thereof, and a fluoronylidene methane compound and a derivative thereof. Specific examples of the heterocyclic compound include a thiadiazopyridine compound and a derivative thereof, a pyrrolopyridine compound and a derivative thereof, a germacyclopentadiene compound and a derivative thereof, a benzazole compound and a derivative thereof, and a terrylendmide compound and a derivative thereof.

Examples of the p-type organic material layer (organic dye material or organic transparent material) forming the second buffer layer include an alicyclic compound, an aromatic ring compound, and a heterocyclic compound in addition to a p-type organic light-absorbing material or organic transparent material other than the above organic light-absorbing material or organic transparent material or the like of the present disclosure. Specific examples of the alicyclic compound include a cyclopentadiene compound a derivative thereof. Specific examples of the aromatic ring compound include a tetraphenyl butadiene compound and a derivative thereof, a p-phenylene compound and a derivative thereof, and a fluoronylidene methane compound and a derivative thereof. Specific examples of the heterocyclic compound include a thiadiazopyridine compound and a derivative thereof, a pyrrolopyridine compound and a derivative thereof, a germacyclopentadiene compound and a derivative thereof, a benzazole compound and a derivative thereof, and a terrylenimide compound and a derivative thereof. In addition, specific examples of the other compounds include a metal typified by Ca, Mg, Li, Ag, or Al and inorganic compounds of these metals (specifically, halides, oxides, and complex compounds of these metals).

Alternatively, in the photoelectric conversion element or the like of the present disclosure, a hole blocking layer/the photoelectric conversion material layer/an electron blocking layer can be formed between the first electrode and the second electrode. Specifically, for example, the following configuration can be used.

the hole blocking layer:

a p-type organic material layer (organic dye material or organic transparent material)

the photoelectric conversion material layer:

the p-type organic light-absorbing material of the present disclosure, or the n-type organic light-absorbing material of the present disclosure, or a mixed material of the p-type organic light-absorbing material of the present disclosure and an n-type organic transparent material, or a mixed material of the n-type organic light-absorbing material of the present disclosure and a p-type organic transparent material, or a bulk hetero layer the electron blocking layer:

an n-type organic material layer (organic dye material or organic transparent material)

Examples of the p-type organic material layer (organic dye material or organic transparent material) forming the hole blocking layer include an alicyclic compound, an aromatic ring compound, and a heterocyclic compound in addition to a p-type organic light-absorbing material or organic transparent material other than the above organic light-absorbing material or organic transparent material or the like of the present disclosure. Specific examples of the alicyclic compound include a cyclopentadiene compound a derivative thereof. Specific examples of the aromatic ring compound include a tetraphenyl butadiene compound and a derivative thereof, a p-phenylene compound and a derivative thereof, and a fluoronylidene methane compound and a derivative thereof. Specific examples of the heterocyclic compound include a thiadiazopyridine compound and a derivative thereof, a pyrrolopyridine compound and a derivative thereof, a germacyclopentadiene compound and a derivative thereof, a benzazole compound and a derivative thereof, and a terrylenimide compound and a derivative thereof. In addition, specific examples of the other compounds include a metal typified by Ca, Mg, Li, Ag, or Al and inorganic compounds of these metals (specifically, halides, oxides, and complex compounds of these metals).

Examples of the organic light-absorbing material or the organic transparent material forming the photoelectric conversion material layer include an aromatic ring compound, a hydrazone compound, an alicyclic compound, an aromatic ring compound, and a heterocyclic compound in addition to the organic light-absorbing material or organic transparent material or the like of the present disclosure, and a p-type organic light-absorbing material or organic transparent material and/or an n-type organic light-absorbing material or organic transparent material other than the above organic light-absorbing material or organic transparent material or the like of the present disclosure. Specific examples of the aromatic ring compound include a monoamine compound and a derivative thereof, an alkylene bond compound and a derivative thereof, an arylene bond compound and a derivative thereof, a phenylenesiamine compound and a derivative thereof, and a starburst compound and a derivative thereof. Specific examples of the alicyclic compound include a cyclopentadiene compound a derivative thereof. Specific examples of the aromatic ring compound include a tetraphenyl butadiene compound and a derivative thereof, a p-phenylene compound and a derivative thereof, and a fluoronylidene methane compound and a derivative thereof. Specific examples of the heterocyclic compound include a thiadiazopyridine compound and a derivative thereof, a pyrrolopyridine compound and a derivative thereof, a germacyclopentadiene compound and a derivative thereof, a benzazole compound and a derivative thereof, and a terrylenimide compound and a derivative thereof.

Examples of the n-type organic material (organic dye material or organic transparent material) forming the electron blocking layer include an aromatic ring compound and a hydrazone compound in addition to an n-type organic light-absorbing material or organic transparent material other than the above organic light-absorbing material or organic transparent material or the like of the present disclosure. Specific examples of the aromatic ring compound include a monoamine compound and a derivative thereof, an alkylene bond compound and a derivative thereof, an arylene bond compound and a derivative thereof, a phenylenesiamine compound and a derivative thereof, and a starburst compound and a derivative thereof. In addition, specific examples of the other compounds include a metal typified by Ca, Mg, Li, Ag, or Al and inorganic compounds of these metals (specifically, halides, oxides, and complex compounds of these metals).

Alternatively, in the photoelectric conversion element or the like of the present disclosure, a form in which a lamination structure of an n-type first photoelectric conversion material layer and a p-type second photoelectric conversion material layer (formed of the organic light-absorbing material of the present disclosure) is formed between the first electrode/the first buffer layer and the second buffer layer/the second electrode, or a form in which this lamination structure is repeatedly formed can be used. A form in which a lamination structure of the n-type first photoelectric conversion material layer (formed of the organic light-absorbing material of the present disclosure) and the p-type second photoelectric conversion material layer is formed between the first electrode/the first buffer layer and the second buffer layer/the second electrode, or a form in which this lamination structure is repeatedly formed can be used. Examples of a material forming these layers include the materials described above.

In addition, a form in which a lamination structure of an n-type first photoelectric conversion material layer, a bulk hetero layer, and a p-type second photoelectric conversion material layer is formed between the first electrode/the first buffer layer and the second buffer layer/the second electrode, or a form in which this lamination structure is repeatedly formed can be used. A form in which a lamination structure of an n-type first photoelectric conversion material layer, a bulk hetero layer, and a p-type second photoelectric conversion material layer (including at least one of the organic light-absorbing materials of the present disclosure) is formed between the first electrode/the first buffer layer and the second buffer layer/the second electrode, or a form in which this lamination structure is repeatedly formed can be used. A form in which a lamination structure of an n-type first photoelectric conversion material layer (including at least one of the organic light-absorbing materials of the present disclosure), a bulk hetero layer, and a p-type second photoelectric conversion material layer is formed between the first electrode/the first buffer layer and the second buffer layer/the second electrode, or a form in which this lamination structure is repeatedly formed can be used.

In addition, a so-called tandem structure obtained by laminating the photoelectric conversion element of the present disclosure having a sensitivity to red, the photoelectric conversion element of the present disclosure having a sensitivity to green, and the photoelectric conversion element of the present disclosure having a sensitivity to blue can be used.

In the photoelectric conversion element or the like of the present disclosure including the preferable embodiment and configuration described above, the first electrode formed of a transparent conductive material can be formed on a transparent substrate, the photoelectric conversion material layer can be formed on the first electrode, and the second electrode can be formed on the photoelectric conversion material layer. Alternatively, the first electrode can be formed on a substrate, the photoelectric conversion material layer can be formed on the first electrode, and the second electrode formed of a transparent conductive material can be formed on the photoelectric conversion material layer. Here, the first electrode and the second electrode are apart from each other, and examples of such a state apart from each other include a form in which the second electrode is disposed above the first electrode.

Examples of a method for forming the photoelectric conversion material layer include various CVD methods including a coating method, a PVD method, and an MOCVD method. Here, specific examples of the coating method include a spin coating method; an immersion method; a casting method; various printing methods such as a screen printing method, an inkjet printing method, an offset printing method, or a gravure printing method; a stamping method; a spraying method; and various coating methods such as an air doctor coater method, a blade coater method, a rod coater method, a knife coater method, a squeeze coater method, a reverse roll coater method, a transfer roll coater method, a gravure coater method, a kiss coater method, a cast coater method, a spray coater method, a slit orifice coater method, or a calendar coater method. Incidentally, in the coating method, examples of a solvent include an organic solvent having a no polarity or low polarity, such as toluene, chloroform, hexane, or ethanol. However, the solvent is not limited thereto. Furthermore, examples of the PVD method include various vacuum vapor deposition methods such as an electron beam heating method, a resistance heating method, or a flash vapor deposition method; a plasma vapor deposition method; various sputtering methods such as a bipolar sputtering method, a DC sputtering method, a DC magnetron sputtering method, a high frequency sputtering method, a magnetron sputtering method, an ion beam sputtering method, or a bias sputtering method; and various ion plating methods such as a DC (direct current) method, an RF method, a multi-cathode method, an activation reaction method, an electric field vapor deposition method, a high-frequency ion plating method, or a reactive, ion plating method. Alternatively, when the photoelectric conversion element or the like is integrated as a photoelectric conversion element forming the solid-state imaging device, it is also possible to use a method for forming a pattern on the basis of a PLD method (pulse laser deposition method).

The thickness of the photoelectric conversion material layer is not limited, but is for example, from $1 \times 10^{-8}$ m to $5 \times 10^{-7}$ m, preferably from $2.5 \times 10^{-8}$ m to $3 \times 10^{-7}$ m, more preferably from $2.5 \times 10^{-8}$ m to $2 \times 10^{-7}$ m, and still more preferably from $1 \times 10^{-7}$ m to $1.8 \times 10^{-7}$ m.

Examples of the substrate include an organic polymer (having a form of a polymer material such as a plastic film, a plastic sheet, or a plastic substrate formed of a polymer material and having flexibility) such as polymethyl methacrylate (polymethyl methacrylate, PMMA), polyvinyl alcohol (PVA), polyvinyl phenol (PVP), polyether sulfone (PBS), polyimide, polycarbonate (PC), polyethylene terephthalate (PET), or polyethylene naphthalate (PEN), and mica. By using such a substrate formed of a polymer material having flexibility, for example, an electronic device can be incorporated or integrated into an electronic device having a curved surface. Alternatively, examples of the substrate include various glass substrates, various glass substrates each having an insulating film formed on a surface thereof, a quartz substrate, a quartz substrate having an insulating film formed on a surface thereof, a silicon substrate having an insulating film formed on a surface thereof, and a metal substrate formed of various alloys such as stainless steel or various metals. Incidentally, examples of the insulating film include a silicon oxide material (for example, $SiO_X$ or spin-on glass (SOG)); silicon nitride ($SiN_Y$); silicon oxynitride (SiON); aluminum oxide ($Al_2O_3$); and a metal oxide and a metal salt. It is also possible to use a conductive substrate having these insulating films formed on a surface thereof (a substrate formed of a metal such as gold or aluminum or a substrate formed of a highly oriented graphite). The surface of the substrate is desirably smooth, but may have roughness to such a degree not to adversely affect characteristics of the photoelectric conversion material layer. By forming a silanol derivative by a silane coupling method, forming a thin film formed of a thiol derivative, a carboxylic acid derivative, a phosphoric acid derivative, or the like by a SAM method or the like, or forming a thin film formed of an insulating metal salt or metal complex by a CVD method or the like on a surface of the substrate, adhesiveness between the first electrode and the substrate or between the second electrode and the substrate may be improved. The transparent substrate means a substrate formed of a material not excessively absorbing light incident on the photoelectric conversion material layer through the substrate.

In some cases, the electrodes or the photoelectric conversion material layer may be coated with a coating layer. Examples of a material forming the coating layer include not only an inorganic insulating material exemplified by a silicon oxide material; silicon nitride ($SiN_Y$); or a metal oxide high dielectric insulating film such as aluminum oxide ($Al_2O_3$), but also include an organic insulating material (organic polymer) exemplified by a straight chain hydrocarbon having a functional group capable of bonding to an electrode at one end, such as polymethyl methacrylate (PMMA); polyvinyl phenol (PVT); polyvinyl alcohol (PVA); polyimide; polycarbonate (PC); polyethylene terephthalate (PET); polystyrene; a silanol derivative (silane coupling agent) such as N-2 (aminoethyl) 3-aminopropyltrimethoxysilane (AEAPTMS), 3-mercaptopropyltrimethoxysilane (MPTMS), or octadecyl trichlorosilane (OTS); octadecanethiol, or dodecyl isocyanate. A combination thereof can be also used. Incidentally, examples of the silicon oxide material include silicon oxide ($SiO_X$) BPSG, PSG, BSG, AsSG, PbSG, silicon oxynitride (SiON), spin on glass (SOG), low dielectric constant material (for example, polyaryl ether, cyclo perfluorocarbon polymer and benzocyclobutene, a cyclic fluorocarbon resin, polytetrafluoroethylene, fluorinated aryl ether, fluorinated polyimide, amorphous carbon, and organic SOG).

The solid-state imaging device may be a front surface-irradiation type or a back surface-irradiation type, and a single-plate color solid-state imaging device can be formed. In addition, a solid-state imaging element may include an on-chip micro lens and a light-shielding layer, if necessary, and includes a driving circuit or wiring for driving the photoelectric conversion element (solid-state imaging element). If necessary, a shutter for controlling incidence of light on the photoelectric conversion element may be disposed, or an optical cut filter may be disposed according to a purpose of the solid-state imaging device. Furthermore, when the solid-state imaging element in the solid-state imaging device of the present disclosure is formed of a single layer of the photoelectric conversion element of the present disclosure, examples of an array of the photoelectric conversion element include a Bayer array, an interline array, a G stripe RB checkered array, a G stripe RB complete checkered array, a checkered complementary color array, a stripe array, a diagonal stripe array, a primary color chrominance array, a field chrominance sequential array, a frame chrominance sequential array, a MOS-type array, an improved MOS-type array, a frame interleaved array, and a field interleaved array. Incidentally, the photoelectric conversion element or the like of the present disclosure can form an optical sensor, an image sensor, or a solar cell in addition to an imaging device such as a TV camera (solid-state imaging device).

Example 1

Figure 3:
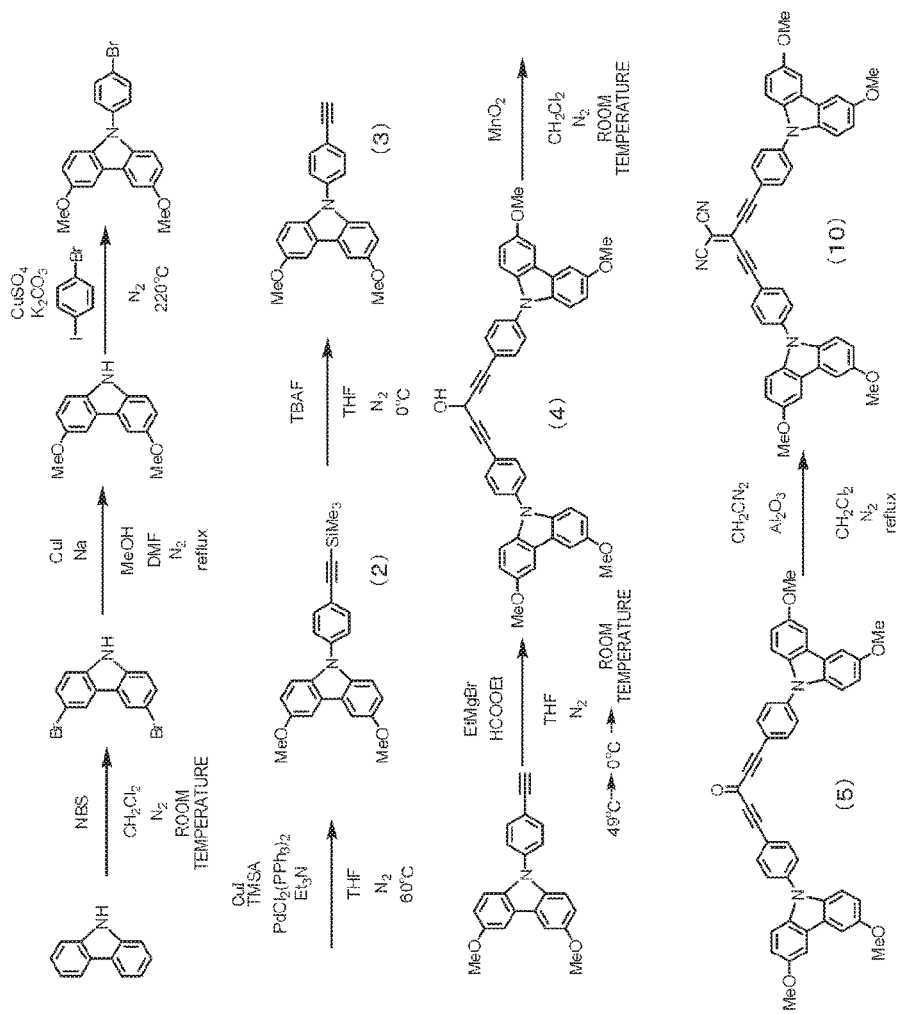
FIG. 3 is a diagram illustrating a scheme for synthesizing a malonotrile/carbazole organic light-absorbing material having a malononitrile/carbazole skeleton represented by formula (10) in Example 1.
Figure 4:
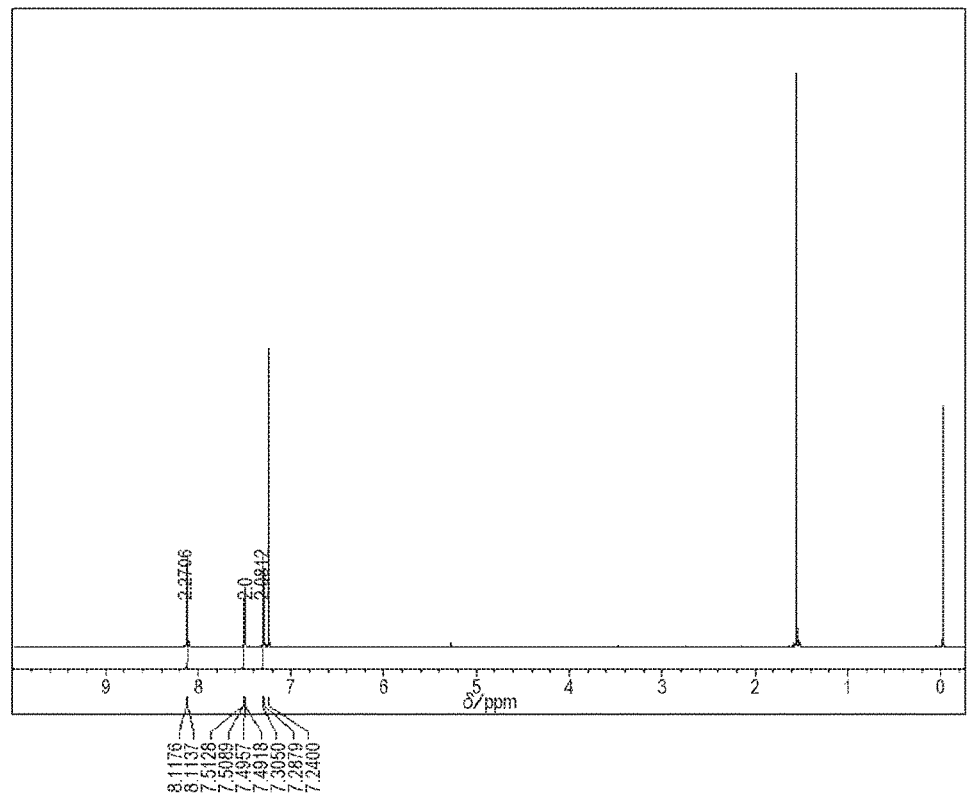
FIG. 4 is $^1$H NMR spectral data of 3,6-dibromo-9H-carbazole.

Example 1 relates to the organic light-absorbing material of the present disclosure and the organic light-absorbing material intermediate thereof. In Example 1, a malononitrile (dicyanoethylene)/carbazole organic light-absorbing material having a malononitrile (dicyanoethylene)/carbazole skeleton represented by the following formula (10) was synthesized on the basis of a scheme described below. The entire scheme is illustrated in FIG. 3. That is, the organic light-absorbing material represented by formula (10) is widely represented by the above structural formula (1). In addition, $R_1$, $R_2$, $R_3$ and $R_4$ are each independently an alkoxy group, and $R_1$, $R_2$, $R_3$ and $R_4$ satisfy $R_1=R_3=R_2=R_4$. Furthermore, $R_1$, $R_2$, $R_3$, and $R_4$ are each a methoxy group. Alternatively, $R_1$, $R_2$, $R_3$, and $R_4$ satisfy $R_1=R_3$ and $R_2=R_4$, and furthermore, $R_1=R_3=R_2=R_4$. Thermal stability can be improved by the malononitrile skeleton (dicyanoethylene skeleton) represented by "A" in formula (10). Crystallinity can be improved by the carbazole skeleton represented by "B". Furthermore, the malononitrile skeleton represented by "A" and the carbazole skeleton represented by "B" have different HOMO levels and LUMO levels from each other. Therefore, on the basis of behavior as an electron donor/electron acceptor or an electron acceptor/electron donor in the same molecule for each of the malononitrile skeleton represented by "A"/the carbazole skeleton represented by "B", exhibited by bonding in a π conjugated system, an interaction of the donor/acceptor is generated, and a strong absorption characteristic can be obtained.

at room temperature overnight while the mixture was shielded from light. After completion of the reaction, silica gel was removed by suction filtration with a Kiriyana funnel, and the filtrate was concentrated with an evaporator. The resulting crude product was purified by silica gel column chromatography (activity I, hexane:dichloromiane=1:2) to obtain a transparent crystal of 3,6-dibromo-9H-carbazole at a yield of 92%. FIG. 4 illustrates spectral data of $^1$H NMR.

$R_f$=0.53 (hexane/CH$_2$Cl$_2$=1:2)

$^1$H NMR (500 MHz, CDCl$_3$): δ=7.30 (d, J=8.6 Hz, 2H), 7.50 (dd, J=8.6, 2.0 Hz, 2H), 8.12 (d, J=1.9 Hz, 2H)

Synthesis of 3,6-dimethoxy-9H-carbazole

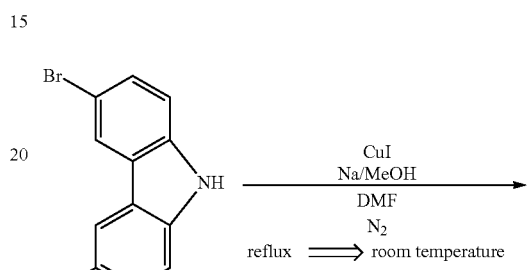

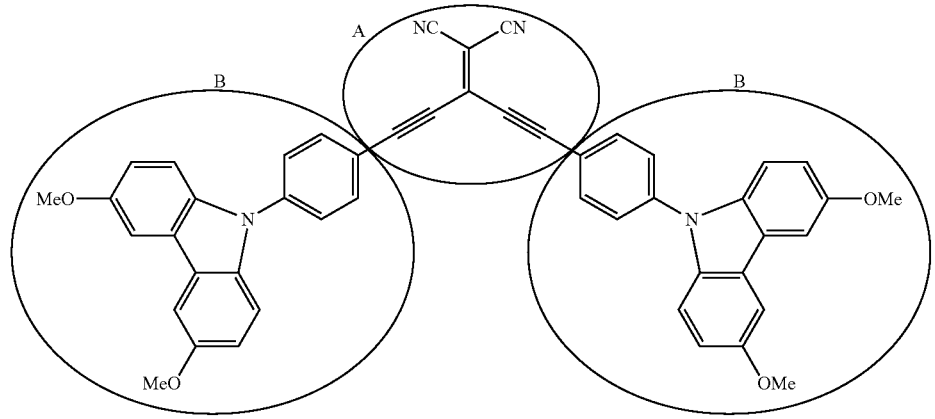

(10)

Synthesis of 3,6-bromo-9H-carbazole

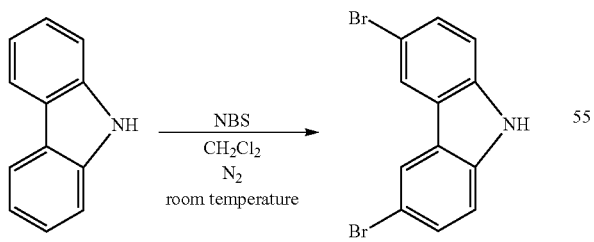

-continued

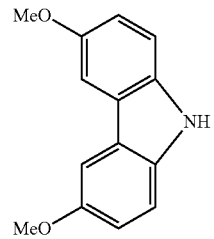

Figure 5:
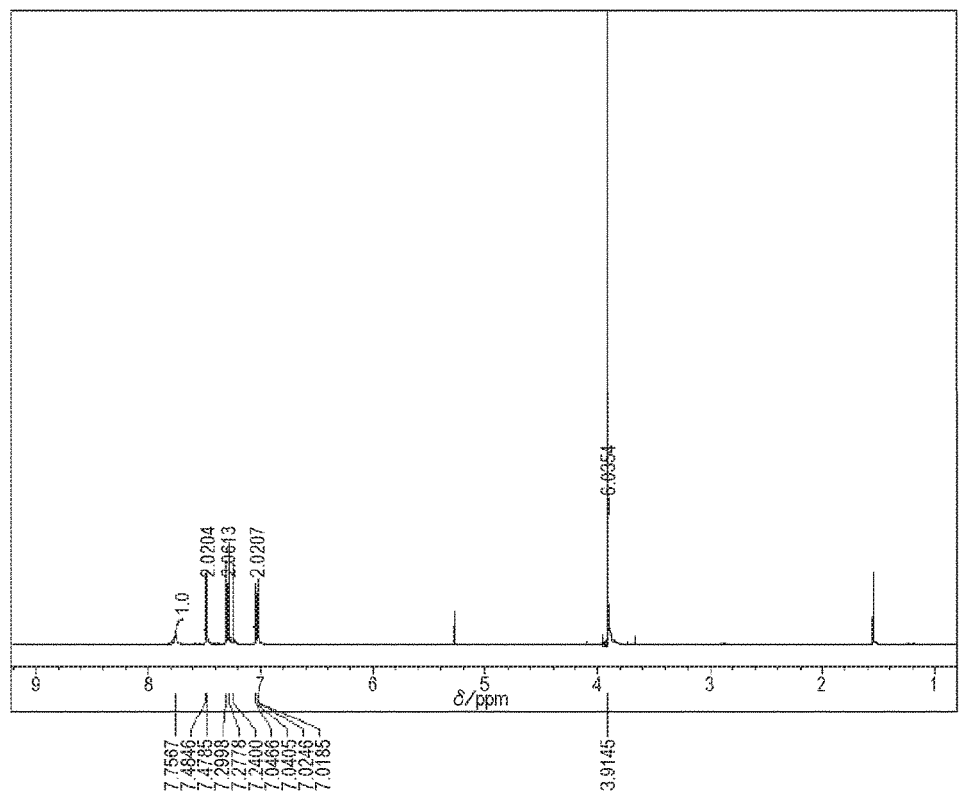
FIG. 5 is $^1$H NMR spectral data of 3,6-dimethoxy-9H-carbazole.

Carbazole (5.02 g, 30.0 mmol) was suspended in 300 ml of dichloromethane together with 60 g of silica gel under a nitrogen atmosphere to obtain a suspension. Then, N-bromosuccinimide (10.7 g, 60.0 mmol) was dissolved in 300 ml of dichloromethane. The resulting mixture was added to the suspension by cannulation. The resulting mixture was stirred The resulting 3,6-dibromo-9H-carbazole (2.4 g, 7.38 mmol) and copper iodide(I) (4.1 g, 22 mmol) were dissolved in 40 ml of methanol under a nitrogen atmosphere. A metal sodium piece (3.4 g, 147.80 mmol) was added thereto slowly to generate sodium methoxide. Thereafter, 20 ml of DMF was added thereto, and the resulting mixture was stirred for three hours while the mixture was heated under reflux. Subsequently, the mixture was removed from an oil bath, and the temperature thereof was returned to room temperature. Thereafter, 100 ml of ethyl acetate was added thereto, and the resulting mixture was stirred. Then, the reaction solution was subjected to celite filtration to remove a metal residue, and was extracted with ethyl acetate. The organic layer was washed with water and subsequently with a saturated salt solution, and then was dried over anhydrous sodium sulfate. The resulting solution was filtered off, and then the filtrate was concentrated with an evaporator. The resulting crude product was purified by silica gel column chromatography (activity I, hexane:dichlormethane=1:3) to obtain a white solid of 3,6-dimethoxy-9H-carbazole at a yield of 88%. FIG. 5 illustrates spectral data of $^1$H NMR.

$R_f$=0.25 (hexane/CH$_2$Cl$_2$=1:3)

$^1$H NMR (400 MHz, CDCl$_3$): δ=3.91 (s, 6H), 7.03 (dd, J=8.8, 2.4 Hz, 4H), 7.29 (d, J=8.8 Hz, 2H), 7.48 (d, C=2.4 Hz, 2H), 7.76 (s, 1H)

Synthesis of 9-(4-bromophenyl) 3,6-dimethoxy-9H-carbazole

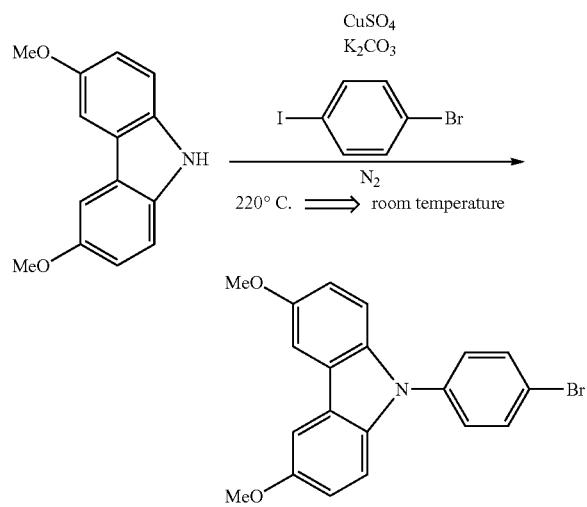

Figure 6:
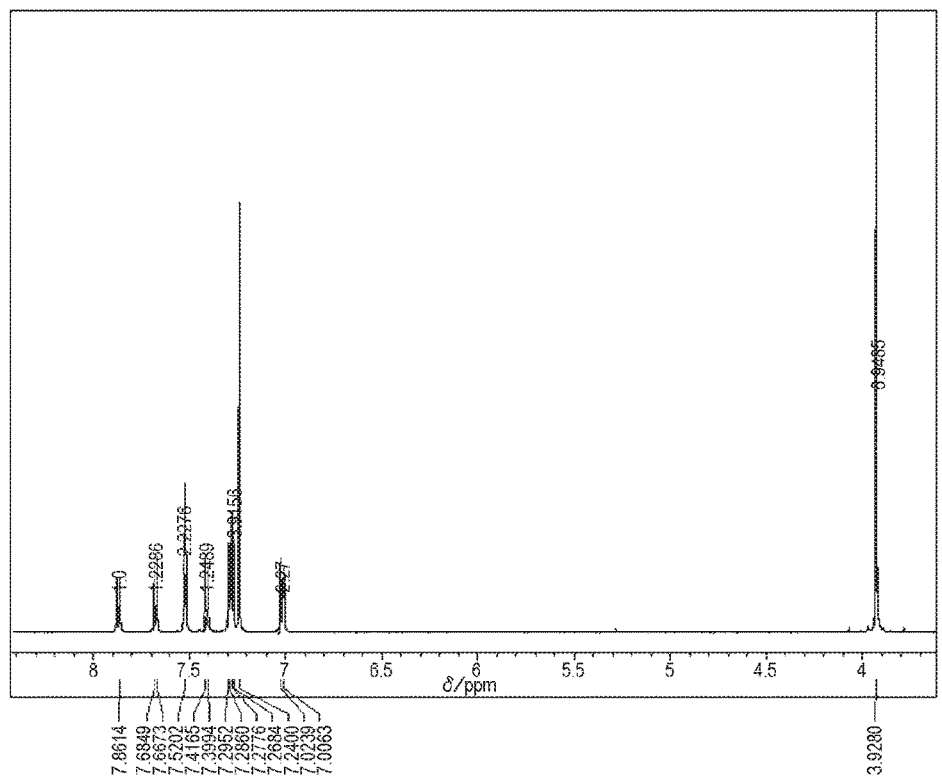
FIG. 6 is $^1$H NMR spectral data of 9-(4-bromophenyl) 3,6-dimethoxy-9H-carbazole.

The resulting 3,6-dimethoxy-9H carbazole (1.1 g, 5.0 mmol), p-bromoiodobenzene (2.7 g, 9.2 mmol), copper sulfide pentahydrate (0.063 g, 0.025 mmol), and potassium carbonate (0.69 g, 5.0 mmol) were put into a three-necked flask under a nitrogen atmosphere, was heated to 220° C. with a mantle heater, and was stirred for three hours. Subsequently, the three-necked flask was removed from the mantle heater, the temperature was returned to room temperature, and water was added thereto to stop the reaction. Then, the resulting solution was extracted with ethyl acetate and was washed. Thereafter, the organic layer was dried over anhydrous magnesium sulfate. Subsequently, the resulting solution was filtered off, and then the filtrate was concentrated with an evaporator. The resulting crude product was purified by silica gel column chromatography (activity I, hexane:dichloromethane=1:2) to obtain a transparent solid of 9-(4-bromophenyl) 3,6-dimethoxy-9H-carbazole at a yield of 64%. FIG. 6 illustrates spectral data of $^1$H NMR.

$R_f$=0.40 (hexane/CH$_2$Cl$_2$=1:2)

$^1$H NMR (500 MHz, CDCl$_3$): δ=3.92 (s, 6H), 7.02 (d, J=8.8 Hz, 2H), 7.28 (dd, J=8.8, 4.6 Hz, 3H), 7.41 (d, J=8.6 Hz, 1H) 7.52 (dd, J=2.1, 2.1 Hz, 2H), 7.68 (d, 8.8 Hz, 1H), 7.87 (d, J=8.6 Hz, 1H)

Synthesis of 9-(4-ethynylphenyl)-3,6-dimethoxy-9H-carbazole

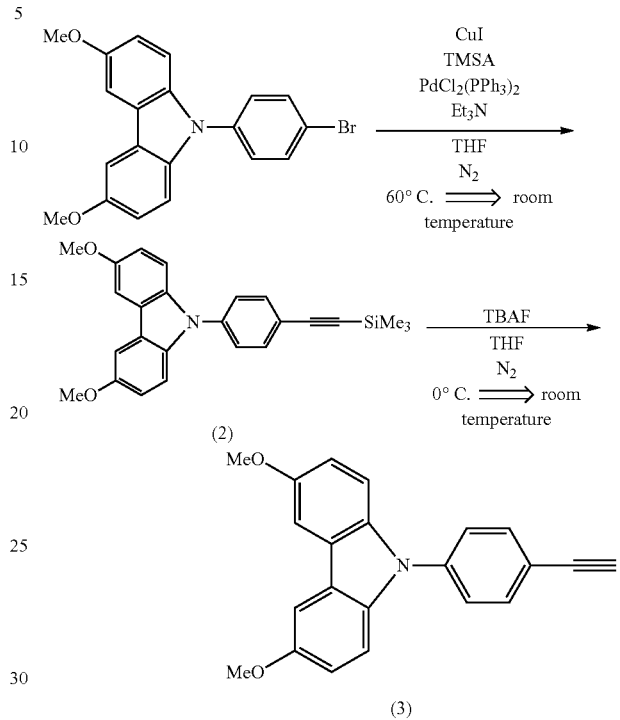

The resulting 9-(4-bromophenyl) 3,6-dimethoxy-9H-carbazole (1.5 g, 4.0 mmol), bis (triphenylphosphine)palladium (II) (0.2 g, 28 mmol), and copper iodide(I) (0.057 g, 0.29 mmol) were suspended in 10 ml of THF under a nitrogen atmosphere, and 20 ml of triethylamine was further added thereto. Trimethylsilyl acetylene (0.8 ml, 5.66 mmol) was dropwise added thereto, and the resulting mixture was stirred overnight while the mixture was heated under reflux at 60° C. Thereafter, the temperature was returned to room temperature, and the solution was concentrated with an evaporator. It was possible to obtain a trimethylsilyl protection body of 9-(4-ethynylphenyl)-3,6-dimethoxy-9H-carbazole as the organic light-absorbing material intermediate according to the first aspect of the present disclosure, formed of the above structural formula (2) at a crude yield of 92%.

Figure 7:
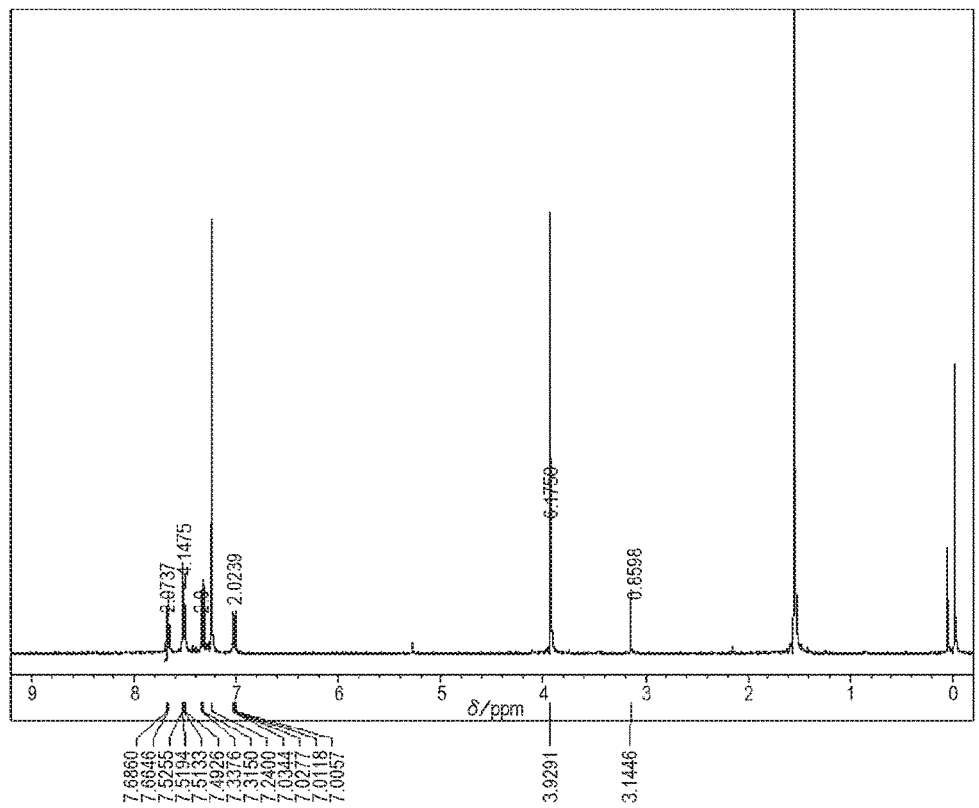
FIG. 7 is $^1$H NMR spectral data of 9-(4-ethynylphenyl)-3,6-dimethoxy-9H-carbazole.

Then, this product itself was used for the following reaction without being purified. That is, the trimethylsilyl protection body of 9-(4-ethynylphenyl)-3,6-dimethoxy-9H-carbazole (about 1.4 g) was dissolved in 40 ml of THF, and was stirred in an ice bath at 0° C. Subsequently, 5.0 ml of tribromo ammonium fluoride (1 mol/liter THF solution) was dropwise added thereto slowly, and the resulting mixture was stirred for three hours in the ice bath. Thereafter, the temperature was returned to room temperature, and the reaction substance was concentrated with an evaporator. The resulting crude product was purified by alumina column chromatography (activity I, hexane:dichloromethane=2:1) to obtain a yellow solid of 9-(4-ethynylphenyl)-3,6-dimethoxy-9H-carbazole as the organic light-absorbing material intermediate according to the second aspect of the present disclosure, formed of the above structural formula (3) at a yield of 98%. FIG. 7 illustrates spectral data of $^1$H NMR.

$R_f$=0.48 (hexane/CH$_2$Cl$_2$=2:1)

$^1$H NMR (400 MHz, CDCl$_3$): δ=3.14 (s, 1H), 3.92 (s, 6H), 1.02 (dd, J=8.8, 2.4 Hz, 2H), 7.33 (d, J=9.0 Hz, 2H), 7.48-7.53 (m, 4H), 7.68 (d, J=8.6 Hz, 2H)

Synthesis of 1,5-bis(4-(3,6-dimethoxy-9H-carbazol-9-yl)phenyl)penta-1,4-diyne-3-yl

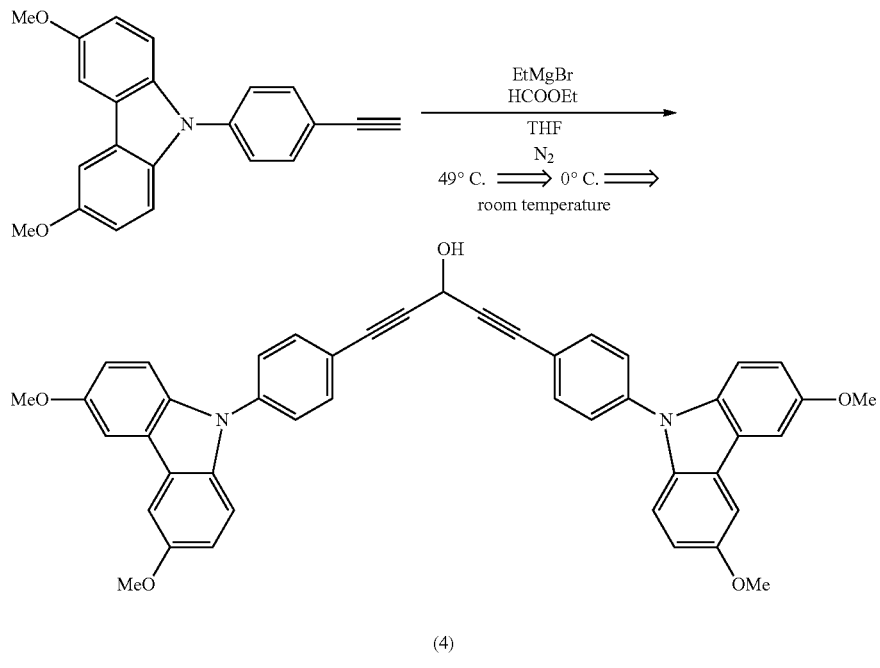

(4)

Figure 8:
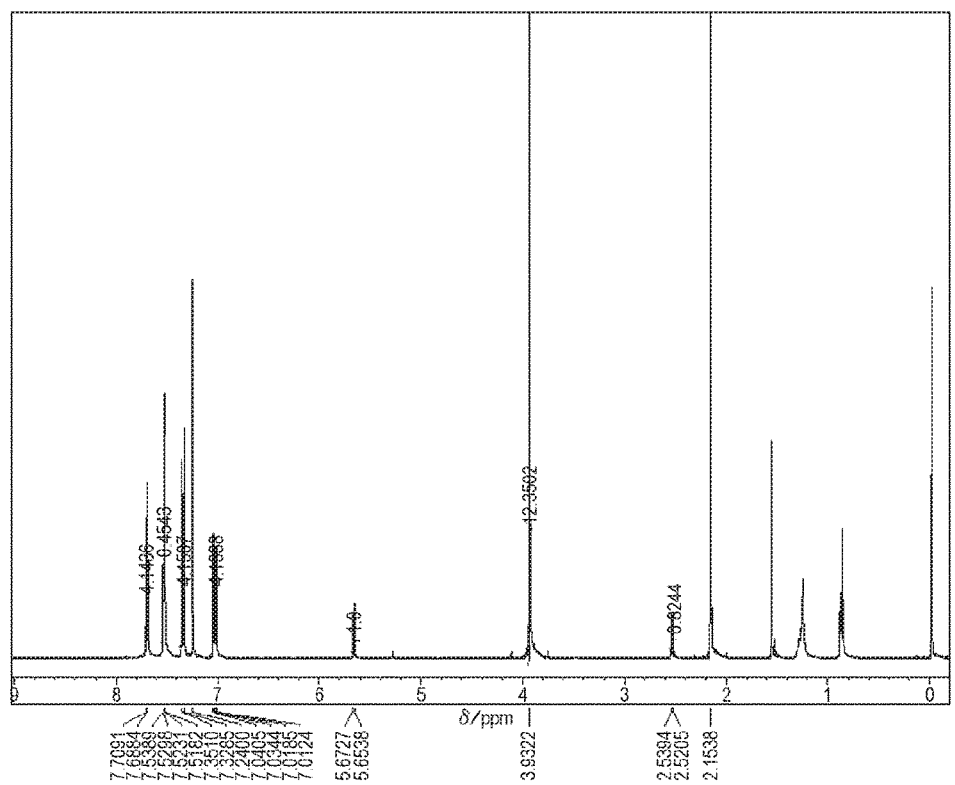
FIG. 8 is $^1$H NMR spectral data of 1,5-bis(4-(3,6-dimethoxy-9H-carbazol-9-yl)phenyl)penta-1,4-diyne-3-ol.

The resulting 9-(4-ethynylphenyl)-3,6-dimethoxy-9H-carbazole (1.63 g, 5.0 mmol) was dissolved in 30 ml of THF under a nitrogen atmosphere. The temperature thereof was raised to 49° C. by an oil bath, and the mixture was stirred. Then, ethylmagnesium bromide (1 mol/liter THF solution, 5.0 ml, 5.0 mmol) was dropwise added thereto, and the resulting mixture was stirred for 45 minutes. Thereafter, the temperature of the reaction solution was lowered to 0° C. by an ice bath, and then ethyl formate (0.2 ml, 2.5 mmol) was dropwise added thereto slowly. Thereafter, the temperature was gradually returned to room temperature. Then, the solution was stirred for five hours, and 20 ml of a saturated ammonium chloride aqueous solution was added thereto to stop the reaction. Then, the solution was extracted with ether, and was washed with a saturated sodium bicarbonate aqueous solution. Thereafter, the organic layer was dried over anhydrous magnesium sulfate. Subsequently, the resulting solution was filtered off, and then the filtrate was concentrated with an evaporator. The resulting crude product was purified by alumina column chromatography (activity I, hexane dichloromethane=2:3) to obtain a pale yellow needle-like crystal of 1,5-bis(4-(3,6-dimethoxy-9H-carbazol-9-yl)phenyl)penta-1,4-diyne-3-ol as the organic light-absorbing material intermediate according to the third aspect of the present disclosure, formed of the above structural formula (4) at a yield of 40%. FIG. 8 illustrates spectral data of $^1$H NMR.

$R_f$=0.16 (hexane/$CH_2Cl_2$=1:7)

$^1$H NMR (400 MHz, $CDCl_3$): δ=2.53 (d, J=7.6 Hz, 1H), 3.93 (s, 12H), 5.66 (d, J=7.68 Hz, 1H), 7.03 (dd, J=8.8, 2.4 Hz, 4H), 7.34 (d, J=9.0 Hz, 4H), 7.51-7.53 (m, 8H), 7.70 (d, J=8.3 Hz, 4H)

Synthesis of 1,5-bis(4-(3,6-dimethoxy-9H-carbazol-9-yl)phenyl)penta-1,4-diyne-3-on

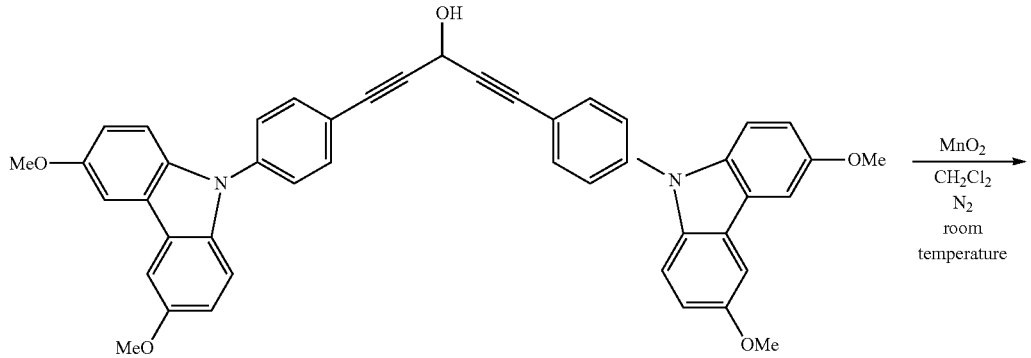

-continued

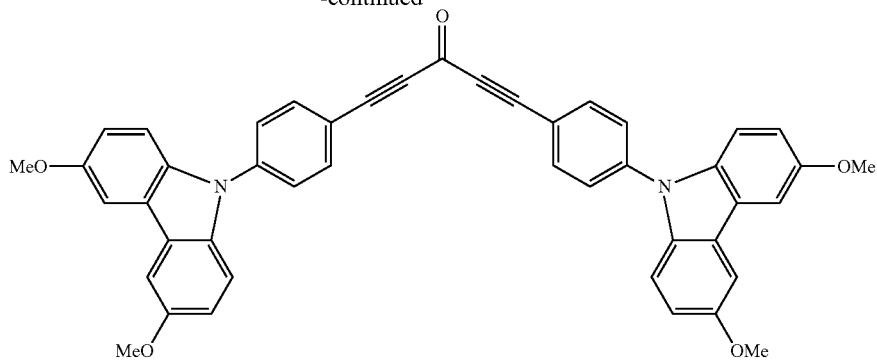

(5)

Figure 9:
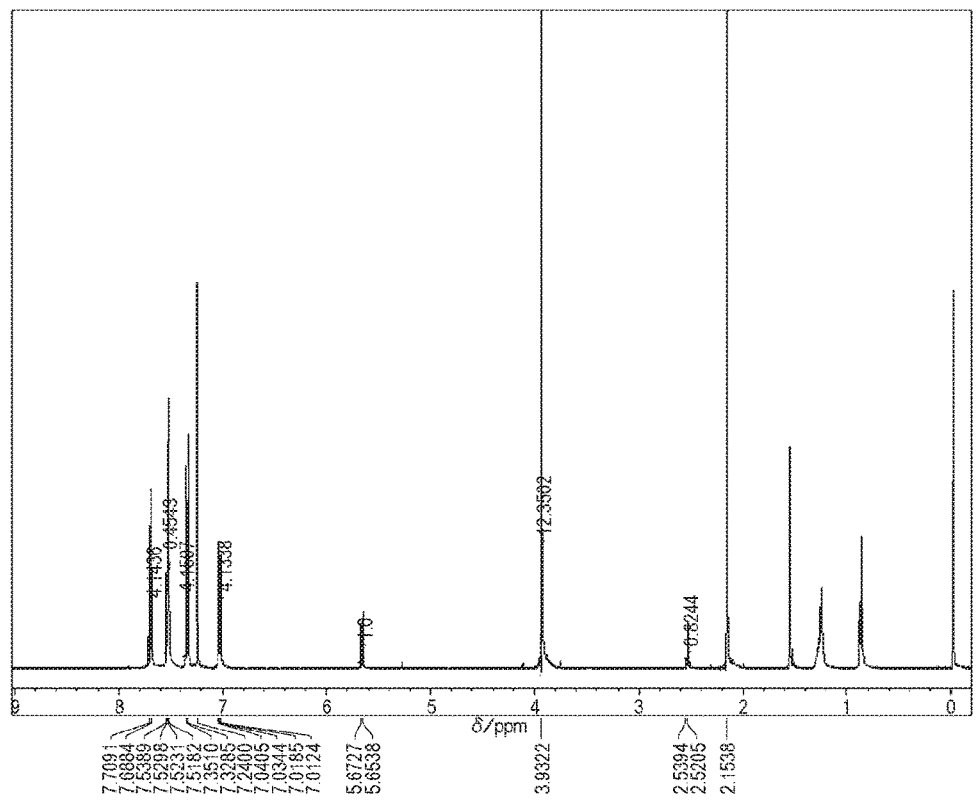

The resulting 1,5-bis(4-(3,6-dimethoxy-9H-carbazol-9-yl)phenyl)penta-1,4-diyne-3-ol (0.49 g, 0.718 mmol) and magnesium oxide(IV) (0.53 g, 6.0 mmol) were suspended in 30 ml of dichloromethane under a nitrogen atmosphere, and the resulting suspension was stirred. After completion of the reaction, the solution was subjected to celite filtration, and the filtrate was concentrated with an evaporator. The resulting crude product was purified by silica gel column chromatography (activity I, hexane:dichloromethane=1:6) to obtain an orange solid of 1,5-bis(4-(3,6-dimethoxy-9H-carbazol-9-yl)phenyl)penta-1,4-diyne-3-on as the organic light-absorbing material intermediate according to the fourth aspect of the present disclosure, formed of the above structural formula (5) at a yield of 98%. FIG. 9 illustrates spectral data of $^1$H NMR.

$R_f$=0.38 (hexane/$CH_2Cl_2$=1:6)
$^1$H NMR (400 MHz, $CDCl_3$): δ=3.93 (s, 12H), 7.04 (dd, J=8.9, 2.8 Hz, 4H), 7.40 (d, J=9.0 Hz, 4H), 7.53 (d, J=2.4 Hz, 4H), 7.64 (d, J=8.6 Hz, 4H), 7.87 (d, J=9.3 Hz, 4H)

[Synthesis of 2-(3-[4-(dimethoxycarbazole)phenyl]-1-{[4-(dimethoxycarbazole)phenyl]ethynyl}-2-ynylidene]

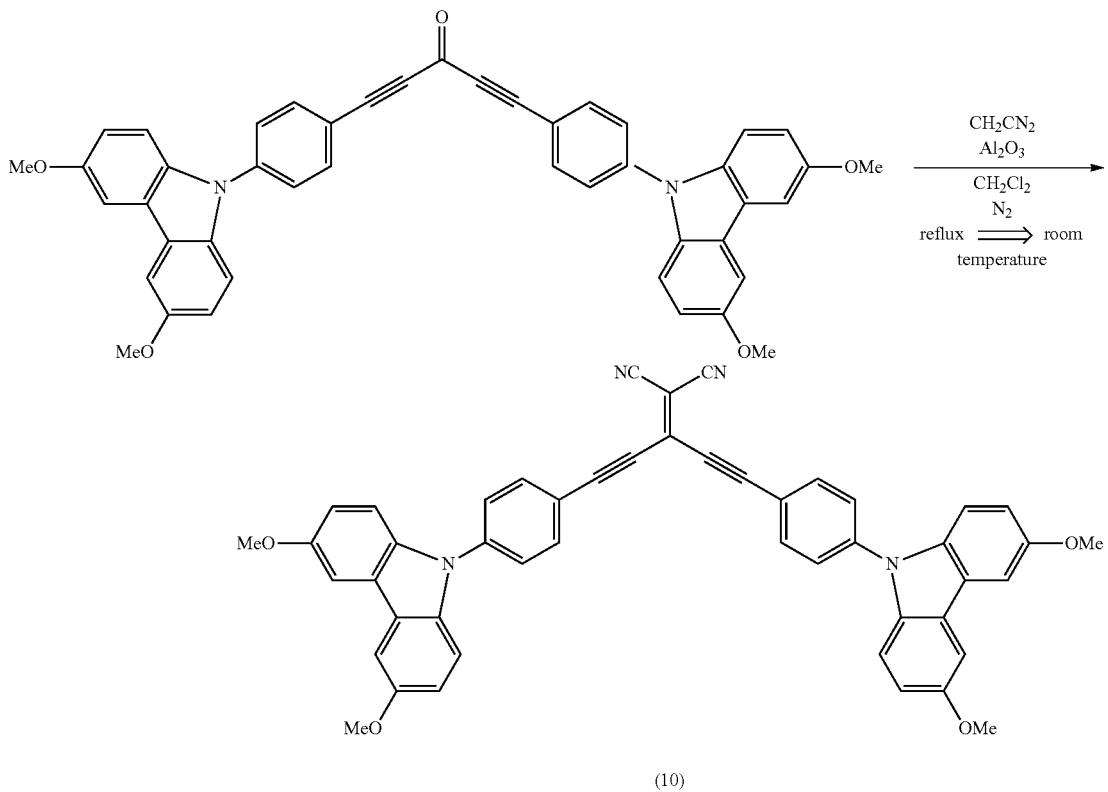

(10)

Figure 10:
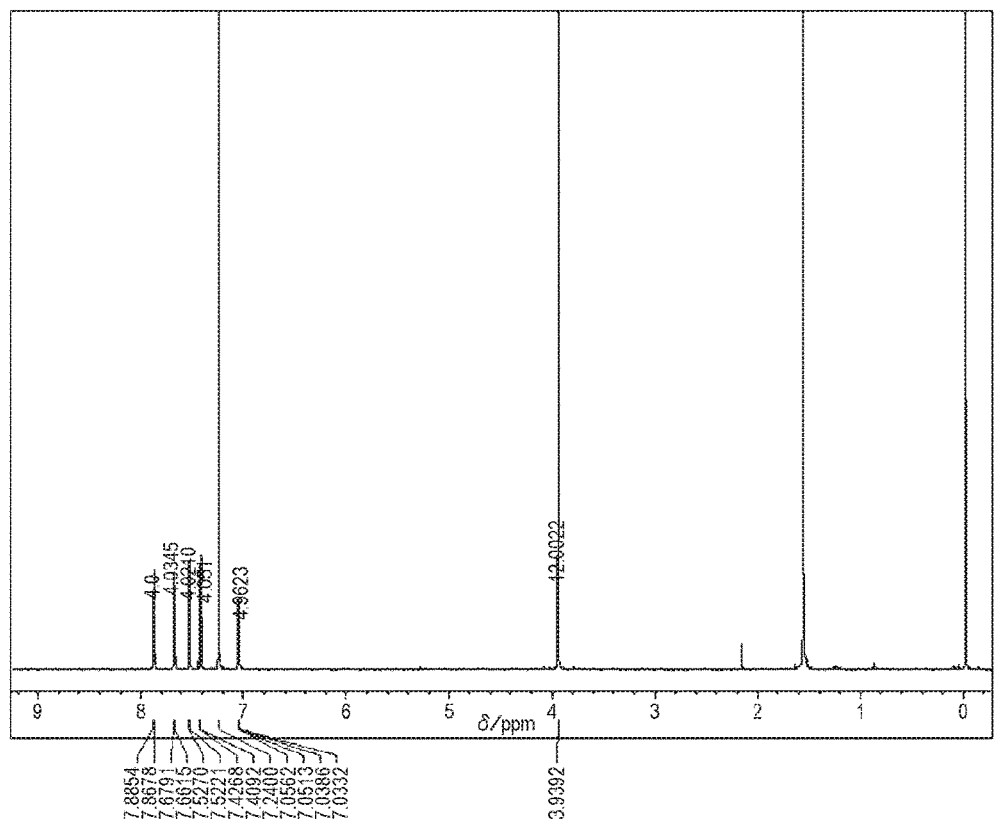
FIG. 10 is $^1$H NMR spectral data of 2-(3-[4-(dimethoxycarbazole)phenyl]-1-{[4-(dimethoxcarbazole)phenyl]ethynyl}-2-ynylidene.

The resulting 1,5-bis(4-(3,6-dimethoxy-9H-carbazol-9-yl)phenyl)penta-1,4-diyne-3-on (374 mg, 0.55 mmol) and malononitrile (109 mg, 1.65 mmol) were dissolved in 20 ml of dichloromethane under a nitrogen atmosphere. The resulting mixture was stirred while the mixture was heated under reflux, 515 mg of alumina oxide (5% by mass, activity II-III)

was directly added thereto, and the resulting mixture was stirred for two hours while the mixture was heated under reflux. After completion of the reaction, the solution was subjected to celite filtration, and the filtrate was concentrated with an evaporator. The resulting crude product was purified by alumina column chromatography (activity I, hexane:dichloromethane=1:4), and was recrystallized with chloroform:methanol to obtain a dark purple crystal of 2-(3-[4-(dimethoxycarbazole)phenyl]-1-{[4-(dimethoxycarbazole)phenyl]ethynyl}-2-ynylidene as the organic light-absorbing material of the present disclosure, formed of the above structural formula (10) (hereinafter, referred to as "substance of structural formula (10)") at a yield of 52%. FIG. 10 illustrates spectral data of $^1$H NMR. Incidentally, a color of the substance of structural formula (10) as a dye was magenta.

$R_f$=0.72 (hexane/$CH_2Cl_2$=1:1)

$^1$H NMR (500 MHz, $CDCl_3$): δ=3.93 (s, 12H), 7.04 (dd, J=9.4, 2.8 Hz, 4H), 7.42 (d, J=8.8 Hz, 4H), 7.52 (d, J=2.5 Hz, 4H), 7.67 (d, J=8.8 Hz, 4H), 7.88 (d, J=8.8 Hz, 4H) m/z value of $C_{48}H_{32}O_3N_4$ by high resolution mass spectrometry (HR-MS)

Calculated value: 728.2424

Measured value: 728.2448

Figure 11:
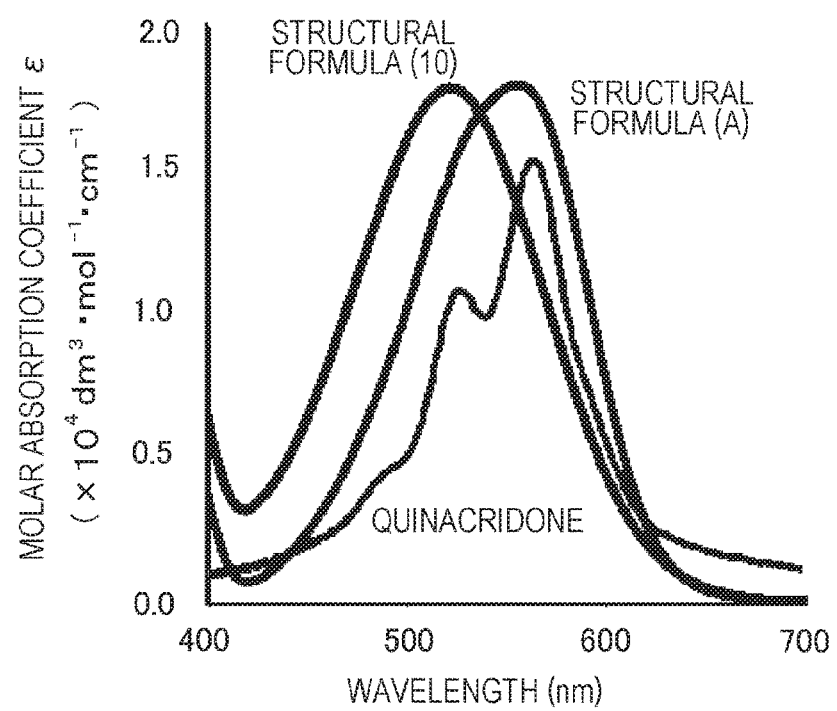
FIG. 11 is a graph illustrating an absorption spectrum of a dichloromethane solution of 2-(3-[4-(dimethoxycarbazole)phenyl]-1-{[4-(dimethoxycarbazole)phenyl]ethynyl}-2-ynylidene.

FIG. 11 illustrates an absorption spectrum of a dichloromethane solution of the resulting substance of structural formula (10). A wavelength ($\lambda_{max}$) of a light absorption peak in the light absorption spectrum of the resulting dichloromethane solution of structural formula (10) (hereinafter, simply referred to as "solution") was 550±50 nm, and was specifically 521 nm. In addition, the light absorption spectrum of the solution had one maximum value in a wavelength range of 500 nm to 600 nm. Furthermore, the molar absorption coefficient ε ($dm^3 \cdot mol^{-1} \cdot cm^{-1}$) of the solution was $1 \times 10^4$ or more, and was specifically $1.77 \times 10^4$. Incidentally, these values of the molar absorption coefficient ε and the absorption coefficient α are almost equal to the values of the molar absorption coefficient ε and the absorption coefficient α of a substance represented by the following structural formula (A) disclosed in JP 2011-199152 A, and are larger than the molar absorption coefficient ε ($dm^3 \cdot mol^{-1} \cdot cm^{-1}$)=$1.4 \times 10^4$ of quinacridone which has been often used conventionally. An absorption cross-sectional area is about two times that of the substance represented by structural formula (A). It has been found that an excellent light absorption characteristic is exhibited.

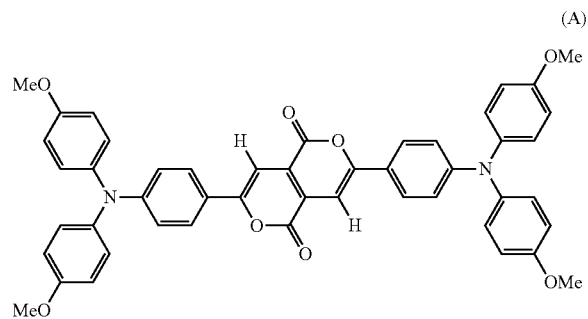 [SMILES: COc1ccc(N(c2ccc(OC)cc2)c2ccc(-c3cc4c(=O)oc(-c5ccc(N(c6ccc(OC)cc6)c6ccc(OC)cc6)cc5)cc4c(=O)o3)cc2)cc1]

(A)

As described above, the malononitrile (dicyanoethylene)/carbazole organic light-absorbing material represented by structural formula (1), forming the photoelectric conversion material layer in Example 1 has a malononitrile skeleton (dicyanoethylene skeleton) and a carbazole skeleton, and therefore can provide an organic material having an excellent light absorption characteristic and can impart an excellent light absorption characteristic to a photoelectric conversion element described next and a solid-state imaging device including the photoelectric conversion element.

Example 2

Example 2 relates to the photoelectric conversion element of the present disclosure and the solid-state imaging device thereof.

As illustrated in the schematic cross sectional view in FIG. 1, the photoelectric conversion element in Example 2 includes:

(a-1) a first electrode 21 and a second electrode 22 disposed apart from each other; and (a-2) a photoelectric conversion material layer 30 disposed between the first electrode 21 and the second electrode 22, and the photoelectric conversion material layer 30 is formed of the above structural formula (1). In addition, the solid-state imaging device in Example 2 includes the photoelectric conversion element in Example 2.

The first electrode 21 which is an electrode on a light incident side is formed of a transparent conductive material, specifically of indium-tin oxide (ITO) having a thickness of 120 nm. The second electrode 22 is formed of aluminum (Al) having a thickness of 100 nm. The first electrode 21 formed of a transparent conductive material is formed on a transparent substrate 20. The photoelectric conversion material layer 30 is formed on the first electrode 21. The second electrode 21 is formed on the photoelectric conversion material layer 30. In this way, the second electrode 22 is disposed above the first electrode 21. Light is incident on the photoelectric conversion material layer 30 through the substrate 20 and the first electrode 21. The substrate 20 is formed of a quartz substrate having a thickness of 0.7 mm. The substrate 20 had a surface roughness of $R_a$=0.28 nm and $R_{max}$=3.3 nm.

A photoelectric conversion element 11 in Example 2 can be manufactured by the following method. That is, first, the first electrode 21 formed of ITO having a thickness of 120 nm is formed on the substrate 20 on the basis of a lithography technique using a photomask. Subsequently, a protrusion 31 formed of an insulating material is formed on the substrate 20 and the first electrode 21. Thereafter, by a vacuum vapor deposition method, the photoelectric conversion material layer 30 (thickness: 100 nm) formed of a malononitrile (dicyanoethylene)/carbazole organic light-absorbing material represented by the above structural formula (10) (exhibiting a p-type conductivity type and acting as a hole supply substance in Example 2) is formed (film-formation) from the first electrode 21 to a top surface of the protrusion 31 on the basis of a vacuum vapor deposition method using a metal mask. The substrate temperature during vacuum vapor deposition was room temperature, and the film-forming rate of the photoelectric conversion material layer 30 was 0.1 nm/s. Subsequently, the second electrode 22 formed of aluminum having a thickness of 100 nm is formed from a top surface of the photoelectric conversion material layer 30 to a top surface of the substrate 20 by a PTO method using a metal mask. As conditions for forming the second electrode 22, the substrate temperature was 30° C., and the film-forming rate of the second electrode 22 was 0.5 nm/s. The protrusion 31 is formed so as to surround a region of the substrate 20 to form the photoelectric conversion material layer 30. The first electrode 21 had a surface roughness of $R_a$=0.3 nm and $R_{max}$=3.8 nm. In addition, before film-formation of the photoelectric conversion material layer 30, the first electrode 21 and the protrusion 31 as base layers were irradiated with an ultraviolet ray and ozone. Incidentally, in general, the surface roughness $R_a$ of the first electrode 21 is desirably 0.3 nm or less.

Figure 2:
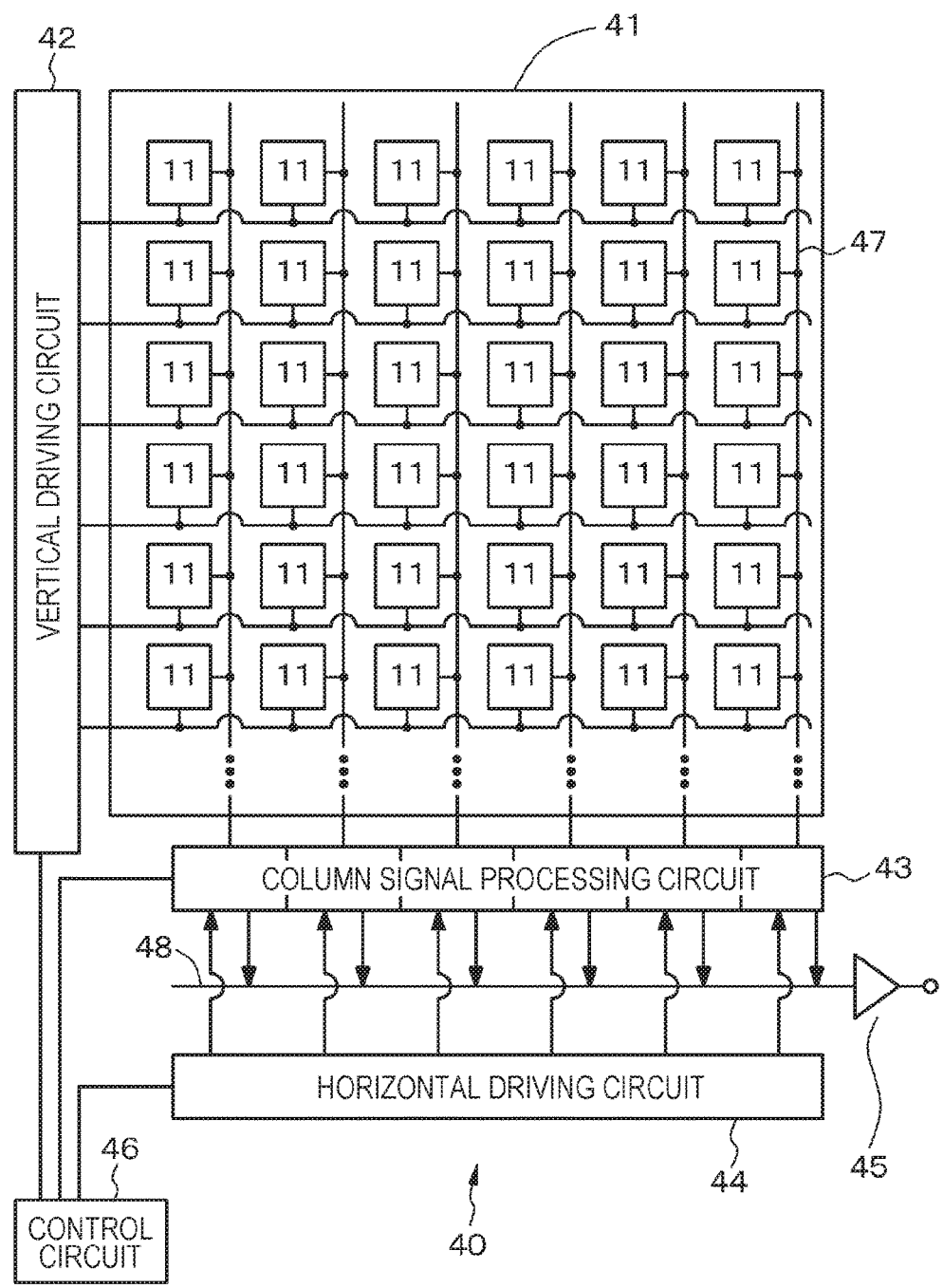
FIG. 2 is a conceptual diagram of a solid-state imaging device in Example 2.

FIG. 2 illustrates a conceptual diagram of the solid-state imaging device (solid-state imaging element) in Example 2. A solid-state imaging device 40 in Example 2 is formed of an imaging area 41 in which the above photoelectric conversion elements 11 are arranged in a two-dimensional array on a semiconductor substrate (for example, Si substrate), and a vertical driving circuit 42, a column signal processing circuit 43, a horizontal driving circuit 44, an output circuit 45, a control circuit 46, and the like as peripheral circuits of the imaging area 41. Incidentally, it is not necessary to say that these circuits can be formed from well-known circuits, and also can be formed using other circuit structures (for example, various circuits used in a conventional CCD imaging device or a CMOS imaging device)

The control circuit 46 generates a clock signal or a control signal as a reference of actions of the vertical driving circuit 42, the column signal processing circuit 43 and the horizontal driving circuit 44 on the basis of a vertical synchronizing signal, a horizontal synchronizing signal, and a master clock. Then, the generated clock signal or control signal is input to the vertical driving circuit 42, the column signal processing circuit 43, and the horizontal driving circuit 44.

For example, the vertical driving circuit 42 is formed of a shift register, and sequentially selects and scans each of the photoelectric conversion elements 11 of the imaging area 41 in a row unit in a vertical direction. Then, a pixel signal based on a current (signal) generated according to the amount of light received by each of the photoelectric conversion elements 11 is sent to the column signal processing circuit 43 through a vertical signal line 47.

For example, the column signal processing circuit 43 is disposed in each column of the photoelectric conversion elements 11. A signal output from the photoelectric conversion elements 11 in one row is subjected to signal processing such as noise removal or signal amplification with a signal from a black reference pixel (not illustrated, but formed around an effective pixel region) for each photoelectric conversion element. In an output stage of the column signal processing circuit 43, a horizontal selection switch (not illustrated) is connected and disposed between the column signal processing circuit 43 and a horizontal signal line 48.

For example, the horizontal driving circuit 44 is formed of a shift register. By sequentially outputting a horizontal scanning pulse, the horizontal driving circuit 44 sequentially selects each of the column signal processing circuits 43, and outputs a signal from each of the column signal processing circuits 43 to the horizontal signal line 48.

The output circuit 45 performs signal processing to a signal sequentially supplied from each of the column signal processing circuits 43 through the horizontal signal line 48, and outputs the signal.

Here, the photoelectric conversion material layer itself also acts as a color filter. Therefore, color separation can be performed even without disposing the color filter.

Hitherto, the present disclosure has been described on the basis of preferable Examples. However, the present disclosure is not limited to these Examples. The structures and configurations, the manufacturing conditions, the manufacturing methods, and the used materials of the photoelectric conversion element and the solid-state imaging device described in Examples are illustrative and can be modified appropriately. For example, by disposing the photoelectric conversion element described in Example 2 on a silicon semiconductor substrate and disposing one or more layers (for example, two layers) of a photoelectric conversion region in the silicon semiconductor substrate located in a lower portion of the photoelectric conversion element, it is possible to obtain a solid-state imaging device having the photoelectric conversion elements (light receiving regions) laminated, that is, having sub-pixels laminated. For example, by receiving green light by the photoelectric conversion element described in Example 2 and disposing one or more layers of a photoelectric conversion region in the silicon semiconductor substrate, such a solid-state imaging device can receive light of another color. Incidentally, instead of disposing the photoelectric conversion region in the silicon semiconductor substrate, the photoelectric conversion region can be formed on a semiconductor substrate by an epitaxial growth method, or can be formed on a silicon layer in a so-called SOI structure. In addition, when the photoelectric conversion element of the present disclosure is caused to act as a solar cell, it is only required to irradiate the photoelectric conversion material layer with light while a voltage is not applied between the first electrode and the second electrode.

Incidentally, the present disclosure may have the following structures.

[A01] <<Photoelectric Conversion Element>>

A photoelectric conversion element including:

(a-1) a first electrode and a second electrode disposed apart from each other; and (a-2) a photoelectric conversion material layer disposed between the first electrode and the second electrode, in which the photoelectric conversion material layer is formed of the following structural formula (1).

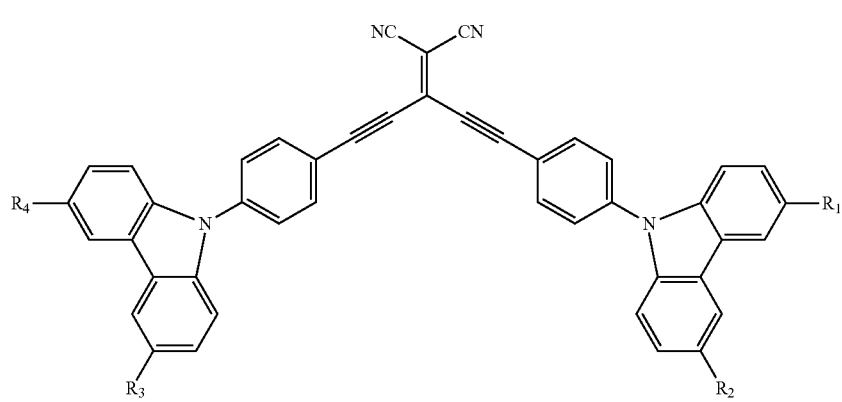

Here, $R_1$, $R_2$, $R_3$ and $R_4$ are each independently a hydrogen atom or a substituent selected from the group consisting of an alkyl group, a cycloalkyl group, an alkenyl group, an alkynyl group, an aryl group, an arylalkyl group, an aromatic heterocyclic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureido group, a sulfinyl group, an alkylsulfonyl group, an arylsulfonyl group, an amino group, a halogen atom, a fluorinated hydrocarbon group, a cyano group, a nitro group, a hydroxy group, a mercapto group, a silyl group, a nitroso group, a cyanide (nitrile) group, an isocyanide (isonitrile) group, a thiocyanate group, an isothiocyanate group, an aldehyde group, a thioaldehyde group, a keto group, thioketo group, and a hydrazide group.

[A02] The photoelectric conversion element according to [A01], in which $R_1$, $R_2$, $R_3$, and $R_4$ are each independently an alkoxy group.

[A03] The photoelectric conversion element according to [A02] in which $R_1$, $R_2$, $R_3$, and $R_4$ satisfy $R_1=R_3=R_2=R_4$.

[A04] The photoelectric conversion element according to [A03], in which $R_1$, $R_2$, $R_3$, and $R_4$ are each a methoxy group.

[A05] The photoelectric conversion element according to [A01], in which $R_1$, $R_2$, $R_3$, and $R_4$ satisfy $R_1=R_3$ and $R_2=R_4$.

[A06] The photoelectric conversion element according to [A05], in which $R_1$, $R_2$, $R_3$, and $R_4$ satisfy $R_1=R_3=R_2=R_4$.

[A07] The photoelectric conversion element according to anyone of [A01] to [A06], In which an electrode on a light incident side is formed of a transparent conductive material.

[A08] The photoelectric conversion element according to any one of [A01] to [A07], in which a wavelength of a light absorption peak in a light absorption spectrum of the photoelectric conversion material layer is 550±50 nm.

[A09] The photoelectric conversion element according to any one of [A01] to [A08], in which the light absorption spectrum of the photoelectric conversion material layer has one maximum value in a wavelength range of 500 nm to 600 nm.

[A10] The photoelectric conversion element according to any one of [A01] to [A09], in which an absorption coefficient of the photoelectric conversion material layer is $1\times10^4$ or more.

[A11] The photoelectric conversion element according to any one of [A01] to [A10], in which a sublimation temperature of a material forming the photoelectric conversion material layer is 250° C. or higher.

[B01] <<Solid-State Imaging Device>>

A solid-state imaging device including:

(a-1) a first electrode and a second electrode disposed apart from each other; and (a-2) a photoelectric conversion material layer disposed between the first electrode and the second electrode, in which the photoelectric conversion material layer includes the photoelectric conversion element formed of the above structural formula (1).

[B02] The solid-state imaging device according to [B01], in which $R_1$, $R_2$, $R_3$, and $R_4$ are each independently an alkoxy group.

[B03] The solid-state imaging device according to [B02], in which $R_1$, $R_2$, $R_3$, and $R_4$ satisfy $R_1=R_3=R_2=R_4$.

[B04] The solid-state imaging device according to [B03], in which $R_1$, $R_2$, $R_3$, and $R_4$ are each a methoxy group.

[B05] The solid-state imaging device according to [B01], in which $R_1$, $R_2$, $R_3$, and $R_4$ satisfy $R_1=R_3$ and $R_2=R_4$.

[B06] The solid-state imaging device according to [B05], in which $R_1$, $R_2$, $R_3$, and $R_4$ satisfy $R_1=R_3=R_2=R_4$.

[B07] The solid-state imaging device according to any one of [B01] to [B06], in which an electrode on a light incident side is formed of a transparent conductive material.

[B08] The solid-state imaging device according to any one of [B01] to [B07], in which a wavelength of a light absorption peak in a light absorption spectrum of the photoelectric conversion material layer is 550±50 nm.

[B09] The solid-state imaging device according to any one of [B01] to [B07], in which the light absorption spectrum of the photoelectric conversion material layer has one maximum value in a wavelength range of 500 nm to 600 nm.

[B10] The solid-state imaging device according to any one of [B01] to [B09], in which an absorption coefficient of the photoelectric conversion material layer is $1\times10^4$ or more.

[B11] The solid-state imaging device according to any one of [B01] to [B10], in which a sublimation temperature of a material forming the photoelectric conversion material layer is 250° C. or higher.

[C01] <<Organic Light-Absorbing Material>>

An organic light-absorbing material formed of the above structural formula (1).

[C02] The organic light-absorbing material according to [C01], in which $R_1$, $R_2$, $R_3$, and $R_4$ are each independently an alkoxy group.

[C03] The organic light-absorbing material according to [C02], in which $R_1$, $R_2$, $R_3$, and $R_4$ satisfy $R_1=R_3=R_2=R_4$.

[C04] The organic light-absorbing material according to [C03], in which $R_1$, $R_2$, $R_3$, and $R_4$ are each a methoxy group.

[C05] The organic light-absorbing material according to [C01], in which $R_1$, $R_2$, $R_3$, and $R_4$ satisfy $R_1=R_3$ and $R_2=R_4$.

[C06] The organic light-absorbing material according to [C05], in which $R_1$, $R_2$, $R_3$, and $R_4$ satisfy $R_1=R_3=R_2=R_4$.

[D01] <<Organic Light-Absorbing Material According to Intermediate: First Aspect>>

An organic light-absorbing material intermediate formed of the following structural formula (2).

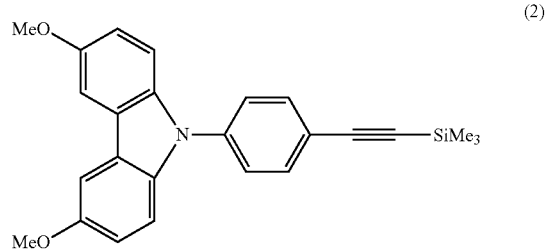 [SMILES: COc1ccc2c(c1)c1cc(OC)ccc1n2-c1ccc(C#C[Si](C)(C)C)cc1]

(2)

[D02] <<Organic Light-Absorbing Material Intermediate: Second Aspect>>

An organic light-absorbing material intermediate formed of the following structural formula (3).

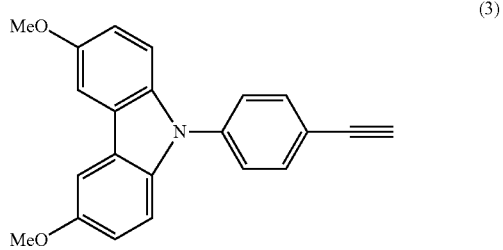 [SMILES: C#Cc1ccc(-n2c3ccc(OC)cc3c3cc(OC)ccc32)cc1]

(3)

[D03] << Organic Light-Absorbing Material Intermediate: Second Aspect>>

An organic light-absorbing material intermediate formed of the following structural formula (4).

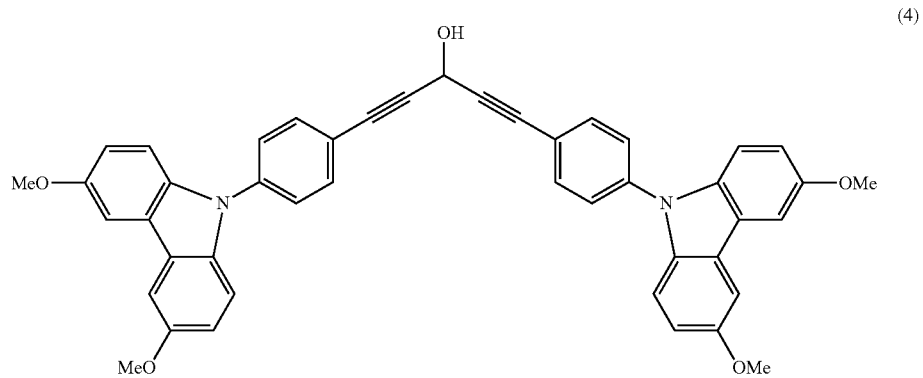 [SMILES: COc1ccc2c(c1)c1cc(OC)ccc1n2-c1ccc(C#CC(O)C#Cc2ccc(-n3c4ccc(OC)cc4c4cc(OC)ccc43)cc2)cc1]

(4)

[D04] << Organic Light-Absorbing Material Intermediate: Fourth Aspect>>

An organic light-absorbing material intermediate formed of the following structural formula (5).

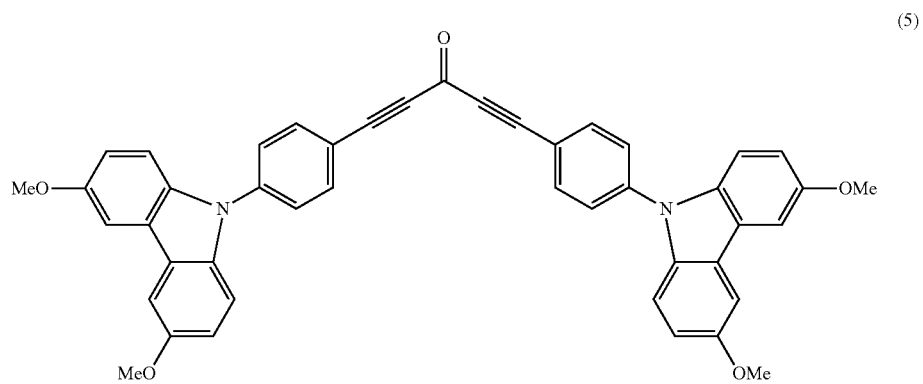 [SMILES: COc1ccc2c(c1)c1cc(OC)ccc1n2-c1ccc(C#CC(=O)C#Cc2ccc(-n3c4ccc(OC)cc4c4cc(OC)ccc43)cc2)cc1]

(5)

REFERENCE SIGNS LIST 11 photoelectric conversion element
20 substrate
21 first electrode
22 second electrode
30 photoelectric conversion material layer
31 protrusion
40 solid-state imaging device
41 imaging area
42 vertical driving circuit
43 column signal processing circuit
44 horizontal driving circuit
45 output circuit
46 control circuit
47 vertical signal line

What is claimed is:

1. A photoelectric conversion element comprising:
   (a-1) a first electrode and a second electrode disposed apart from each other; and
   (a-2) a photoelectric conversion material layer disposed between the first electrode and the second electrode,
   wherein the photoelectric conversion material layer is formed of structural formula (1) below:

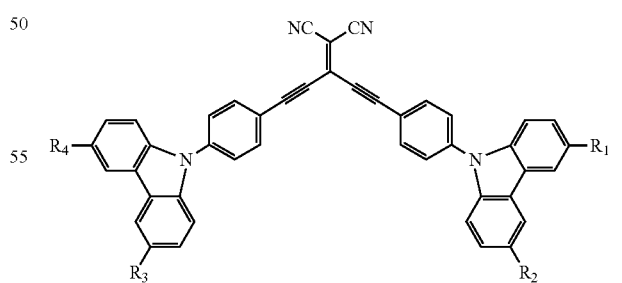

(1)

wherein, $R_1$, $R_2$, $R_3$, and $R_4$ are each independently a hydrogen atom or a substituent selected from the group consisting of an alkyl group, a cycloalkyl group, an alkenyl group, an alkynyl group, an aryl group, an arylalkyl group, an aromatic heterocyclic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureido group, a sulfinyl group, an alkylsulfonyl group, an arylsulfonyl group, an amino group, a halogen atom, a fluorinated hydrocarbon group, a cyano group, a nitro group, a hydroxy group, a mercapto group, a silyl group, a nitroso group, a cyanide (nitrile) group, an isocyanide (isonitrile) group, a thiocyanate group, an isothiocyanate group, an aldehyde group, a thioaldehyde group, a keto group, thioketo group, and a hydrazide group.

2. The photoelectric conversion element of claim 1, wherein $R_1$, $R_2$, $R_3$, and $R_4$ are each independently an alkoxy group.

3. The photoelectric conversion element of claim 2, wherein $R_1$, $R_2$, $R_3$, and $R_4$ satisfy $R_1=R_3=R_2=R_4$.

4. The photoelectric conversion element of claim 3, wherein $R_1$, $R_2$, $R_3$, and $R_4$ are each a methoxy group.

5. The photoelectric conversion element of claim 1, wherein $R_1$, $R_2$, $R_3$, and $R_4$ satisfy $R_1=R_3$ and $R_2=R_4$.

6. The photoelectric conversion element of claim 5, wherein $R_1$, $R_2$, $R_3$, and $R_4$ satisfy $R_1=R_3=R_2=R_4$.

7. The photoelectric conversion element of claim 1, wherein an electrode on a light incident side is formed of a transparent conductive material.

8. The photoelectric conversion element of claim 1, wherein a wavelength of a light absorption peak in a light absorption spectrum of the photoelectric conversion material layer is 550±50 nm.

9. The photoelectric conversion element of claim 8, wherein the light absorption spectrum of the photoelectric conversion material layer has one maximum value in a wavelength range of 500 nm to 600 nm.

10. The photoelectric conversion element of claim 1, wherein an absorption coefficient of the photoelectric conversion material layer is $1\times10^4$ or more.

11. The photoelectric conversion element of claim 1, wherein a sublimation temperature of a material forming the photoelectric conversion material layer is 250° C. or higher.

12. A solid-state imaging device comprising:
(a-1) a first electrode and a second electrode disposed apart from each other; and
(a-2) a photoelectric conversion material layer disposed between the first electrode and the second electrode, wherein the photoelectric conversion material layer includes a photoelectric conversion element formed of structural formula (1) below:

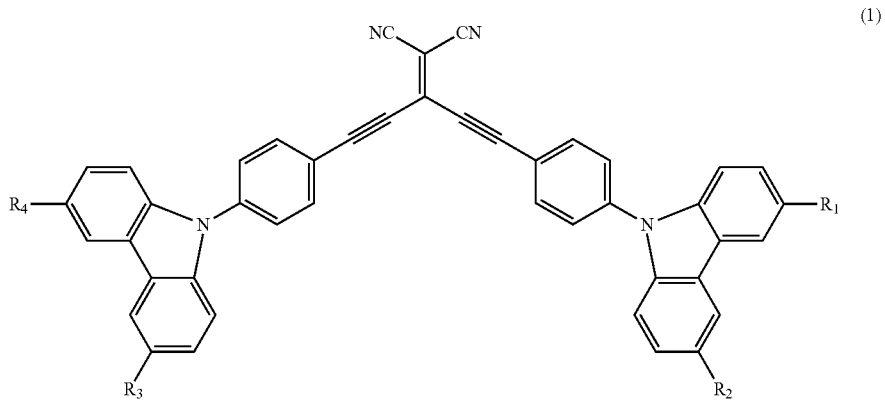

(1)

wherein, $R_1$, $R_2$, $R_3$, and $R_4$ are each independently a hydrogen atom or a substituent selected from the group consisting of an alkyl group, a cycloalkyl group, an alkenyl group, an alkynyl group, an aryl group, an arylalkyl group, an aromatic heterocyclic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureido group, a sulfinyl group, an alkylsulfonyl group, an arylsulfonyl group, an amino group, a halogen atom, a fluorinated hydrocarbon group, a cyano group, a nitro group, a hydroxy group, a mercapto group, a silyl group, a nitroso group, a cyanide (nitrile) group, an isocyanide (isonitrile) group, a thiocyanate group, an isothiocyanate group, an aldehyde group, a thioaldehyde group, a keto group, thioketo group, and a hydrazide group.

* * * * *